(12) United States Patent
Tyler, II et al.

(10) Patent No.: US 11,166,778 B2
(45) Date of Patent: Nov. 9, 2021

(54) MEDICAL DEVICE STABILIZING APPARATUS AND METHOD OF USE

(71) Applicant: Edwards Lifesciences Corporation, Irvine, CA (US)

(72) Inventors: Gregory Scott Tyler, II, Winston-Salem, NC (US); Arnold Cruz Tuason, Claremont, CA (US); David M. Taylor, Lake Forest, CA (US); Matthew T. Winston, Aliso Viejo, CA (US); Alexander J. Siegel, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 284 days.

(21) Appl. No.: 15/951,830

(22) Filed: Apr. 12, 2018

(65) Prior Publication Data

US 2018/0311007 A1 Nov. 1, 2018

Related U.S. Application Data

(60) Provisional application No. 62/491,392, filed on Apr. 28, 2017.

(51) Int. Cl.
*A61B 50/20* (2016.01)
*A61F 2/24* (2006.01)
(Continued)

(52) U.S. Cl.
CPC .............. *A61B 50/20* (2016.02); *A61B 50/15* (2016.02); *A61B 50/30* (2016.02); *A61B 90/50* (2016.02);
(Continued)

(58) Field of Classification Search
CPC ............ A61M 25/02; A61M 2025/024; A61M 2025/028; A61B 1/00147–00149;
(Continued)

(56) References Cited

U.S. PATENT DOCUMENTS 3,874,388 A 4/1975 King et al.
4,001,556 A 1/1977 Folchi et al.
(Continued)

FOREIGN PATENT DOCUMENTS

CN 1142351 A 2/1997
CN 203355093 U 12/2013
(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Catherine B Kuhlman
(74) *Attorney, Agent, or Firm* — Thomas C. Richardson

(57) ABSTRACT

The present disclosure provides a stabilizing unit for a medical device. The stabilizing unit includes a retaining arm having a surface configured to abut a surface of the medical device. The stabilizing unit also includes a stabilizing fork having a slot configured to receive the medical device. A biasing member is in contact with the stabilizing fork and is configured to urge the slot of the stabilizing fork towards the retaining arm. When the medical device is placed in the slot of the stabilizing fork, the basing member urges the stabilizing fork against an adjacent surface of the medical device, and an opposing surface of the medical device against the retaining arm.

47 Claims, 14 Drawing Sheets

(51) Int. Cl.
  *A61M 25/02* (2006.01)
  *A61B 50/15* (2016.01)
  *A61B 50/30* (2016.01)
  *A61B 90/50* (2016.01)
  *A61B 90/57* (2016.01)
  *A61M 5/14* (2006.01)
  *A61B 46/23* (2016.01)

(52) U.S. Cl.
  CPC ............ *A61B 90/57* (2016.02); *A61F 2/2427* (2013.01); *A61M 5/1415* (2013.01); *A61M 25/02* (2013.01); *A61B 46/23* (2016.02); *A61B 2090/508* (2016.02); *A61F 2/24* (2013.01); *A61M 2025/024* (2013.01); *A61M 2025/028* (2013.01); *A61M 2209/084* (2013.01)

(58) Field of Classification Search
  CPC ... A61B 50/15; A61B 50/20–28; A61B 90/11; A61B 90/50–57; A61B 2090/571; A61B 2050/007; A61B 50/30–39; A61B 2050/3002–375; A61F 2002/4622
  See application file for complete search history.

(56) References Cited

U.S. PATENT DOCUMENTS

| | | |
|---|---|---|
| 4,340,091 A | 7/1982 | Skelton et al. |
| 4,365,488 A | 12/1982 | Mochida et al. |
| 4,506,669 A | 3/1985 | Blake, III |
| 4,533,179 A | 8/1985 | Nichols et al. |
| 4,585,443 A | 4/1986 | Kaufman |
| 4,590,937 A | 5/1986 | Deniega |
| 4,686,997 A | 8/1987 | Oloff et al. |
| 4,693,248 A | 9/1987 | Failla |
| 4,803,983 A | 2/1989 | Siegel |
| 4,951,576 A | 8/1990 | Cobos et al. |
| 5,098,048 A | 3/1992 | Chen |
| 5,125,895 A | 6/1992 | Buchbinder et al. |
| 5,171,252 A | 12/1992 | Friedland |
| 5,184,601 A | 2/1993 | Putman |
| 5,195,962 A | 3/1993 | Martin et al. |
| 5,246,109 A | 9/1993 | Markle et al. |
| 5,292,326 A | 3/1994 | Green et al. |
| 5,314,411 A | 5/1994 | Bierman et al. |
| 5,327,905 A | 7/1994 | Avitall |
| 5,359,741 A | 11/1994 | Lang |
| 5,363,861 A | 11/1994 | Edwards et al. |
| 5,370,685 A | 12/1994 | Stevens |
| 5,389,077 A | 2/1995 | Melinyshyn et al. |
| 5,405,110 A | 4/1995 | Mistretta |
| 5,411,552 A | 5/1995 | Andersen et al. |
| 5,413,120 A | 5/1995 | Grant |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,571,072 A | 11/1996 | Kronner |
| 5,586,163 A | 12/1996 | Goldstein |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,876,325 A | 3/1999 | Mizuno et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,332,874 B1 | 12/2001 | Eliasen et al. |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,018,362 B2 | 3/2006 | Bierman et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,220,246 B2 | 5/2007 | Raulerson et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,776,017 B2 | 8/2010 | Ponzi et al. |
| 7,780,723 B2 | 8/2010 | Taylor |
| 7,803,185 B2 | 9/2010 | Gabbay |
| 7,824,443 B2 | 11/2010 | Salahieh et al. |
| 7,950,306 B2 | 5/2011 | Stuart |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,162,898 B1 | 4/2012 | Wright |
| 8,172,856 B2 | 5/2012 | Eigler et al. |
| 8,206,437 B2 | 6/2012 | Bonhoeffer et al. |
| 8,211,064 B2 | 7/2012 | Sloan |
| 8,216,301 B2 | 7/2012 | Bonhoeffer et al. |

(56) References Cited

U.S. PATENT DOCUMENTS

| | | | |
|---|---|---|---|
| 8,277,420 | B2 | 10/2012 | Bierman et al. |
| 8,303,653 | B2 | 11/2012 | Bonhoeffer et al. |
| 8,313,525 | B2 | 11/2012 | Tuval et al. |
| 8,348,995 | B2 | 1/2013 | Tuval et al. |
| 8,348,996 | B2 | 1/2013 | Tuval et al. |
| 8,414,643 | B2 | 4/2013 | Tuval et al. |
| 8,425,404 | B2 * | 4/2013 | Wilson ............... A61B 17/02 600/102 |
| 8,449,599 | B2 | 5/2013 | Chau et al. |
| 8,449,606 | B2 | 5/2013 | Eliasen et al. |
| 8,460,368 | B2 | 6/2013 | Taylor et al. |
| 8,470,028 | B2 | 6/2013 | Thornton et al. |
| 8,480,730 | B2 | 7/2013 | Maurer et al. |
| 8,540,767 | B2 | 9/2013 | Zhang |
| 8,579,965 | B2 | 11/2013 | Bonhoeffer et al. |
| 8,585,756 | B2 | 11/2013 | Bonhoeffer et al. |
| 8,608,705 | B2 | 12/2013 | Peters et al. |
| 8,652,202 | B2 | 2/2014 | Alon et al. |
| 8,668,733 | B2 | 3/2014 | Haug et al. |
| 8,708,952 | B2 | 4/2014 | Cohen et al. |
| 8,721,665 | B2 | 5/2014 | Oz et al. |
| 8,734,400 | B2 | 5/2014 | Ciccone |
| 8,740,918 | B2 | 6/2014 | Seguin |
| 8,771,347 | B2 | 7/2014 | DeBoer et al. |
| 8,778,017 | B2 | 7/2014 | Eliasen et al. |
| 8,808,248 | B2 | 8/2014 | Schultz |
| 8,827,960 | B2 | 9/2014 | Haak |
| 8,834,564 | B2 | 9/2014 | Tuval et al. |
| 8,840,663 | B2 | 9/2014 | Saiahieh et al. |
| 8,876,894 | B2 | 11/2014 | Tuval et al. |
| 8,876,895 | B2 | 11/2014 | Tuval et al. |
| 8,945,177 | B2 | 2/2015 | Dell et al. |
| 9,034,032 | B2 | 5/2015 | McLean et al. |
| 9,056,187 | B2 | 6/2015 | Rosenberg et al. |
| 9,163,893 | B1 | 10/2015 | Gutierrez |
| 9,198,757 | B2 | 12/2015 | Schroeder et al. |
| 9,220,507 | B1 | 12/2015 | Patel et al. |
| 9,247,866 | B2 | 2/2016 | Aferzon |
| 9,259,317 | B2 | 2/2016 | Wilson et al. |
| 9,278,193 | B2 | 3/2016 | Haider et al. |
| 9,282,972 | B1 | 3/2016 | Patel et al. |
| 9,301,834 | B2 | 4/2016 | Tuval et al. |
| 9,308,360 | B2 | 4/2016 | Bishop et al. |
| 9,427,327 | B2 | 6/2016 | Parrish |
| 9,387,071 | B2 | 7/2016 | Tuval et al. |
| 9,398,922 | B2 | 7/2016 | Parihar et al. |
| 9,433,754 | B2 | 9/2016 | Mogg |
| 9,439,763 | B2 | 9/2016 | Geist et al. |
| 9,480,822 | B2 | 11/2016 | Kaiser |
| 9,510,837 | B2 | 12/2016 | Seguin |
| 9,510,946 | B2 | 12/2016 | Chau et al. |
| 9,572,660 | B2 | 2/2017 | Braido et al. |
| 9,642,704 | B2 | 5/2017 | Tuval et al. |
| 9,700,445 | B2 | 7/2017 | Martin et al. |
| 9,775,963 | B2 | 10/2017 | Miller |
| D809,139 | S | 1/2018 | Marsot et al. |
| 9,889,002 | B2 | 2/2018 | Bonhoeffer et al. |
| 9,949,824 | B2 | 4/2018 | Bonhoeffer et al. |
| 10,076,327 | B2 | 9/2018 | Ellis et al. |
| 10,076,415 | B1 | 9/2018 | Metchik et al. |
| 10,099,050 | B2 | 10/2018 | Chen et al. |
| 10,105,221 | B2 | 10/2018 | Siegel |
| 10,105,222 | B1 | 10/2018 | Metchik et al. |
| 10,111,751 | B1 | 10/2018 | Metchik et al. |
| 10,123,873 | B1 | 11/2018 | Metchik et al. |
| 10,130,475 | B1 | 11/2018 | Metchik et al. |
| 10,136,993 | B1 | 11/2018 | Metchik et al. |
| 10,159,570 | B1 | 12/2018 | Metchik et al. |
| 10,226,309 | B2 | 3/2019 | Ho et al. |
| 10,231,837 | B1 | 3/2019 | Metchik et al. |
| 10,238,493 | B1 | 3/2019 | Metchik et al. |
| 10,238,494 | B2 | 3/2019 | McNiven et al. |
| 10,238,495 | B2 | 3/2019 | Marsot et al. |
| 10,299,924 | B2 | 5/2019 | Kizuka |
| 10,376,673 | B2 | 8/2019 | Van Hoven et al. |
| 2001/0005787 | A1 | 6/2001 | Oz et al. |
| 2002/0013571 | A1 | 1/2002 | Goldfarb et al. |
| 2002/0107531 | A1 | 8/2002 | Schreck et al. |
| 2002/0173811 | A1 | 11/2002 | Tu et al. |
| 2002/0177789 | A1 | 11/2002 | Ferry et al. |
| 2002/0183787 | A1 | 12/2002 | Wahr et al. |
| 2003/0081953 | A1 | 5/2003 | Wei |
| 2003/0144573 | A1 | 7/2003 | Heilman et al. |
| 2003/0187467 | A1 | 10/2003 | Schreck |
| 2003/0208231 | A1 | 11/2003 | Williamson et al. |
| 2004/0003819 | A1 | 1/2004 | St. Goar et al. |
| 2004/0034365 | A1 | 2/2004 | Lentz et al. |
| 2004/0044350 | A1 | 3/2004 | Martin et al. |
| 2004/0044365 | A1 | 3/2004 | Bachman |
| 2004/0049207 | A1 | 3/2004 | Goldfarb et al. |
| 2004/0127981 | A1 | 7/2004 | Randert et al. |
| 2004/0127982 | A1 | 7/2004 | Machold et al. |
| 2004/0133078 | A1 | 7/2004 | Edoga et al. |
| 2004/0147943 | A1 | 7/2004 | Kobayashi |
| 2004/0181206 | A1 | 9/2004 | Chiu et al. |
| 2004/0181238 | A1 | 9/2004 | Zarbatany et al. |
| 2004/0210307 | A1 | 10/2004 | Khairkhahan |
| 2004/0220593 | A1 | 11/2004 | Greenhalgh |
| 2004/0267089 | A1 * | 12/2004 | Otsuka ............... A61B 1/042 600/102 |
| 2005/0010287 | A1 | 1/2005 | Macoviak et al. |
| 2005/0049618 | A1 | 3/2005 | Masuda et al. |
| 2005/0137690 | A1 | 6/2005 | Salahieh et al. |
| 2005/0143767 | A1 | 6/2005 | Kimura et al. |
| 2005/0165429 | A1 | 7/2005 | Douglas et al. |
| 2005/0216039 | A1 | 9/2005 | Lederman |
| 2005/0234435 | A1 | 10/2005 | Layer |
| 2005/0251183 | A1 | 11/2005 | Buckman et al. |
| 2005/0288786 | A1 | 12/2005 | Chanduszko |
| 2006/0020275 | A1 | 1/2006 | Goldfarb et al. |
| 2006/0058738 | A1 | 3/2006 | Ponzi et al. |
| 2006/0089671 | A1 | 4/2006 | Goldfarb et al. |
| 2006/0100649 | A1 | 5/2006 | Hart |
| 2006/0122647 | A1 | 6/2006 | Callaghan et al. |
| 2006/0142694 | A1 | 6/2006 | Bednarek et al. |
| 2006/0178700 | A1 | 8/2006 | Quinn |
| 2006/0224169 | A1 | 10/2006 | Weisenburgh et al. |
| 2007/0010800 | A1 | 1/2007 | Weitzner et al. |
| 2007/0010877 | A1 | 1/2007 | Salahieh et al. |
| 2007/0016286 | A1 | 1/2007 | Herrmann et al. |
| 2007/0021779 | A1 | 1/2007 | Garvin et al. |
| 2007/0032807 | A1 | 2/2007 | Ortiz et al. |
| 2007/0055289 | A1 | 3/2007 | Scouten et al. |
| 2007/0093657 | A1 | 4/2007 | Rogers et al. |
| 2007/0093890 | A1 | 4/2007 | Eliasen et al. |
| 2007/0149955 | A1 | 6/2007 | Edoga et al. |
| 2007/0156197 | A1 | 7/2007 | Root et al. |
| 2007/0191154 | A1 | 8/2007 | Genereux et al. |
| 2007/0197858 | A1 | 8/2007 | Goldfarb et al. |
| 2007/0198038 | A1 | 8/2007 | Cohen et al. |
| 2007/0265700 | A1 | 11/2007 | Eliasen et al. |
| 2007/0282414 | A1 | 12/2007 | Soltis et al. |
| 2007/0293943 | A1 | 12/2007 | Quinn |
| 2007/0299387 | A1 | 12/2007 | Williams et al. |
| 2007/0299424 | A1 | 12/2007 | Cumming et al. |
| 2008/0039743 | A1 | 2/2008 | Fox et al. |
| 2008/0039953 | A1 | 2/2008 | Davis et al. |
| 2008/0065149 | A1 | 3/2008 | Thielen et al. |
| 2008/0077144 | A1 | 3/2008 | Crofford |
| 2008/0091169 | A1 | 4/2008 | Heideman et al. |
| 2008/0140089 | A1 | 6/2008 | Kogiso et al. |
| 2008/0147093 | A1 | 6/2008 | Roskopf et al. |
| 2008/0147112 | A1 | 6/2008 | Sheets et al. |
| 2008/0149001 | A1 * | 6/2008 | Hodges ............... A61B 50/13 108/6 |
| 2008/0167713 | A1 | 7/2008 | Bolling |
| 2008/0177300 | A1 | 7/2008 | Mas et al. |
| 2008/0208332 | A1 | 8/2008 | Lamphere et al. |
| 2008/0221672 | A1 | 9/2008 | Lamphere et al. |
| 2008/0255427 | A1 | 10/2008 | Satake et al. |
| 2008/0281411 | A1 | 11/2008 | Berreklouw |
| 2008/0287862 | A1 | 11/2008 | Weitzner et al. |
| 2008/0294247 | A1 | 11/2008 | Yang et al. |
| 2008/0306442 | A1 | 12/2008 | Bardsley et al. |

(56) References Cited

U.S. PATENT DOCUMENTS

| | | |
|---|---|---|
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0216197 A1 | 8/2009 | Russo |
| 2009/0275902 A1 | 11/2009 | Heeps et al. |
| 2009/0287304 A1 | 11/2009 | Dahlgren et al. |
| 2010/0010449 A1 | 1/2010 | Leibowitz et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0160825 A1 | 6/2010 | Parihar et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0001022 A1 | 1/2011 | Edinger |
| 2011/0082538 A1 | 4/2011 | Dahlgren et al. |
| 2011/0130718 A1 | 6/2011 | Kidd et al. |
| 2011/0137410 A1 | 6/2011 | Hacohen |
| 2011/0152779 A1 | 6/2011 | Panotopoulos |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0016312 A1 | 1/2012 | Brown et al. |
| 2012/0022633 A1 | 1/2012 | Olson et al. |
| 2012/0065464 A1 | 3/2012 | Ellis et al. |
| 2012/0069965 A1 | 3/2012 | Scheffer et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0271237 A1* | 10/2012 | Andino ............ A61M 25/02 604/174 |
| 2012/0277853 A1 | 11/2012 | Rothstein |
| 2012/0316505 A1 | 12/2012 | Wright |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0131600 A1 | 5/2013 | Mogg |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0261099 A1* | 9/2014 | Lewis ............ A61B 50/13 108/49 |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0005733 A1 | 1/2015 | Le et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0133958 A1 | 5/2015 | Singh et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheehan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0249991 A1 | 9/2016 | Glozman et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2016/0367332 A1* | 12/2016 | Shah ............ A61B 90/11 |
| 2017/0007101 A1 | 1/2017 | Dejima |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100201 A1 | 4/2017 | Ho et al. |
| 2017/0100236 A1 | 4/2017 | Robertson et al. |
| 2017/0239048 A1 | 8/2017 | Goldfarb et al. |
| 2017/0246435 A1 | 8/2017 | Oveland |
| 2017/0252154 A1 | 9/2017 | Tubishevitz et al. |
| 2017/0265894 A1 | 9/2017 | Mark et al. |
| 2017/0281330 A1 | 10/2017 | Liljegren et al. |
| 2017/0340353 A1 | 11/2017 | Ahluwalia et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |

(56) References Cited

U.S. PATENT DOCUMENTS

| | | |
|---|---|---|
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0108225 A1 | 4/2020 | Jamal et al. |
| 2020/0113683 A1 | 4/2020 | Dale et al. |
| 2020/0230362 A1 | 7/2020 | Basude |
| 2020/0237512 A1 | 7/2020 | McCann et al. |
| 2020/0337842 A1 | 10/2020 | Metchik et al. |

FOREIGN PATENT DOCUMENTS

| | | |
|---|---|---|
| CN | 204337479 U | 5/2015 |
| DE | 102013002813 A1 | 8/2014 |
| EP | 0098100 A2 | 1/1984 |
| FR | 2146050 A5 | 2/1973 |
| FR | 9711600 | 3/1997 |
| KR | 10-0977615 B1 | 8/2010 |
| WO | 8706474 A1 | 11/1987 |
| WO | 03082121 A1 | 10/2003 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018093565 A1 | 5/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34, pp. 343-346. 2009.

Batista RJ et al., "Partial left ventriculectomy to treat end-stage heart disease", Ann Thorac Surg., vol. 64, Issue-3, pp. 634-638, Sep. 1997.

Beall AC Jr, et al.,"Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995;Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue-3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Rashkind et al., "Creation of an Atrial Septal Defect Without Thoracotomy: A Palliative Approach to Complete Transposition of the Great Arteries", The Journal of the American Medical Association; vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Reul RM et al., "Mitral valve reconstruction for mitral insufficiency", Prog Cardiovasc Dis., vol. 39, Issue-6, May-Jun. 1997.

Rosch, M.D., Josef, "The Birth, Early Years and Future of Interventional Radiology," J Vasc Interv Radiol 2003; 14:841-853.

Ross, D.N. "Aortic Valve Surgery", Surgery of the Aortic Valves, Guy's Hospital, London, pp. 192-197.

(56) References Cited

OTHER PUBLICATIONS

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176, pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation, Ann Thorac Surg., vol. 66, Issue-6, pp. 1640-1646, Nov. 1998.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

\* cited by examiner

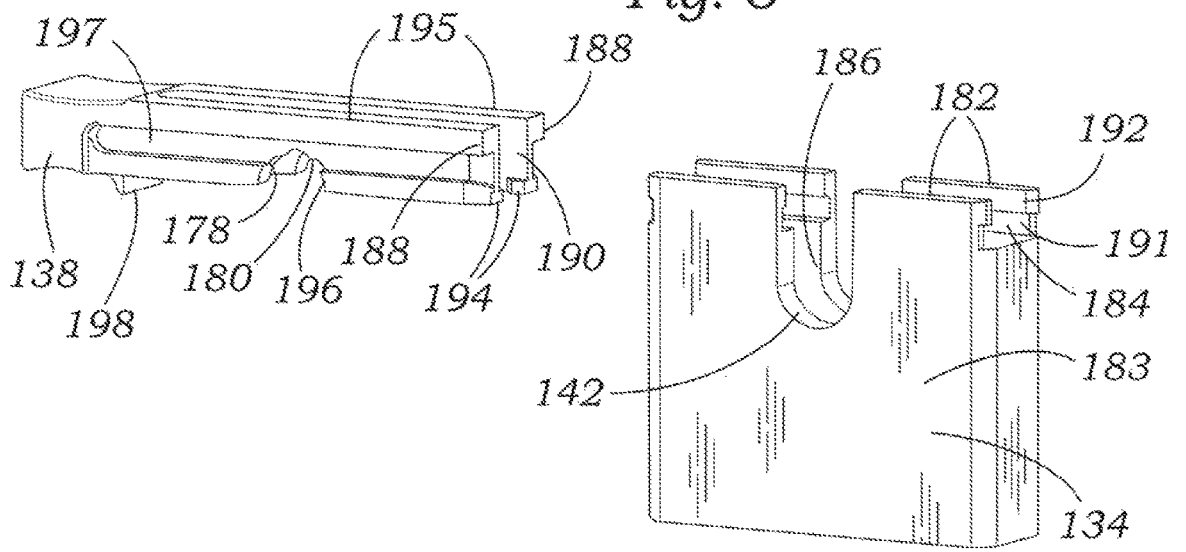
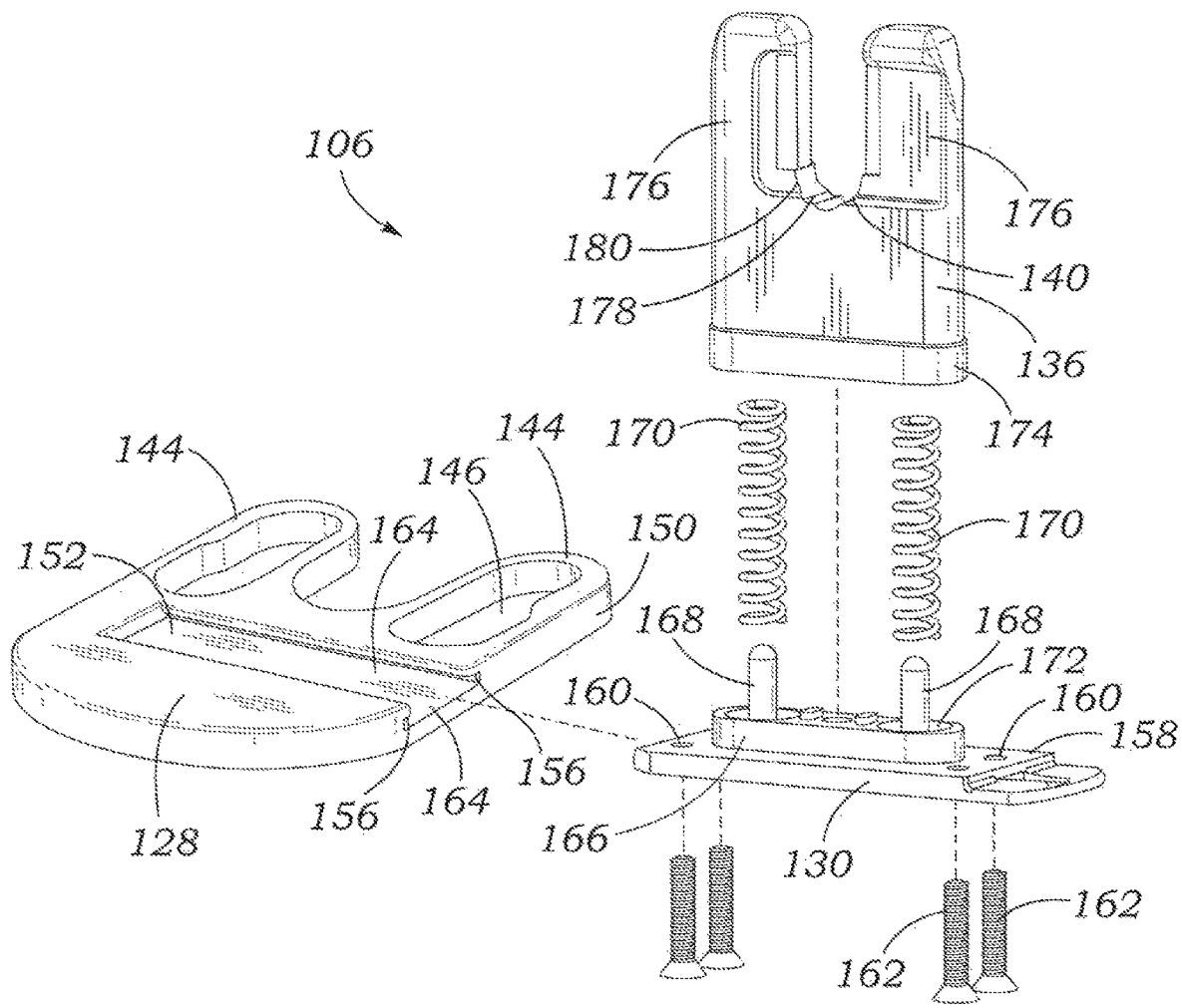
Fig. 3

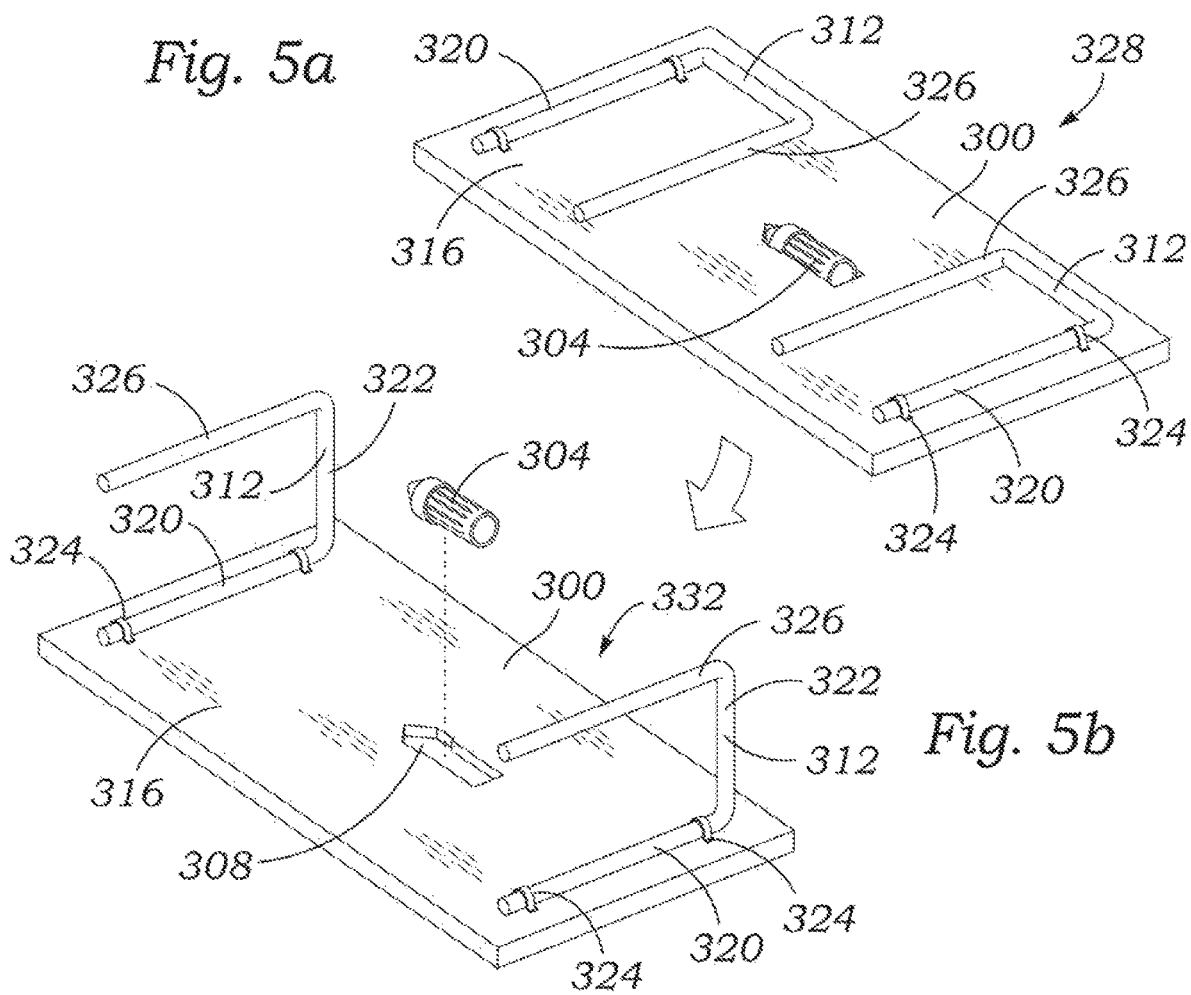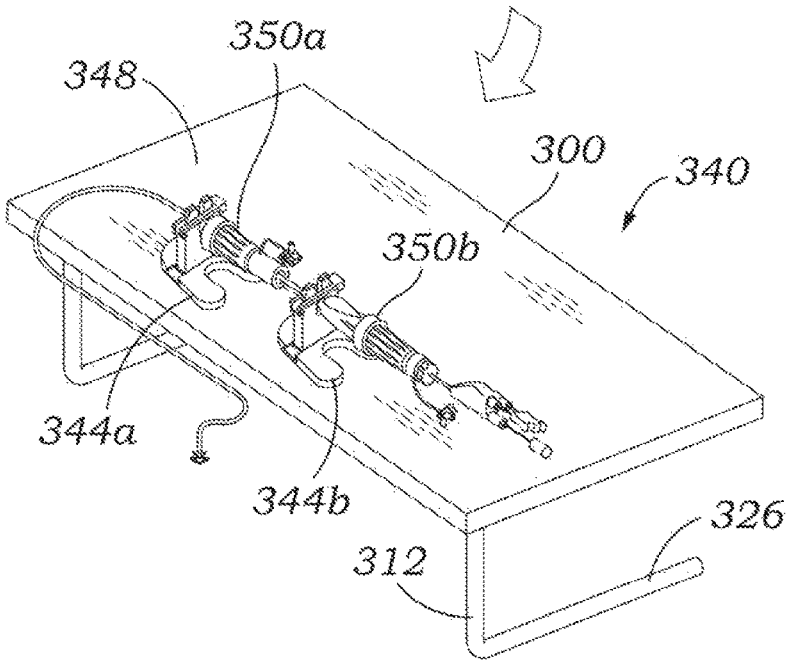

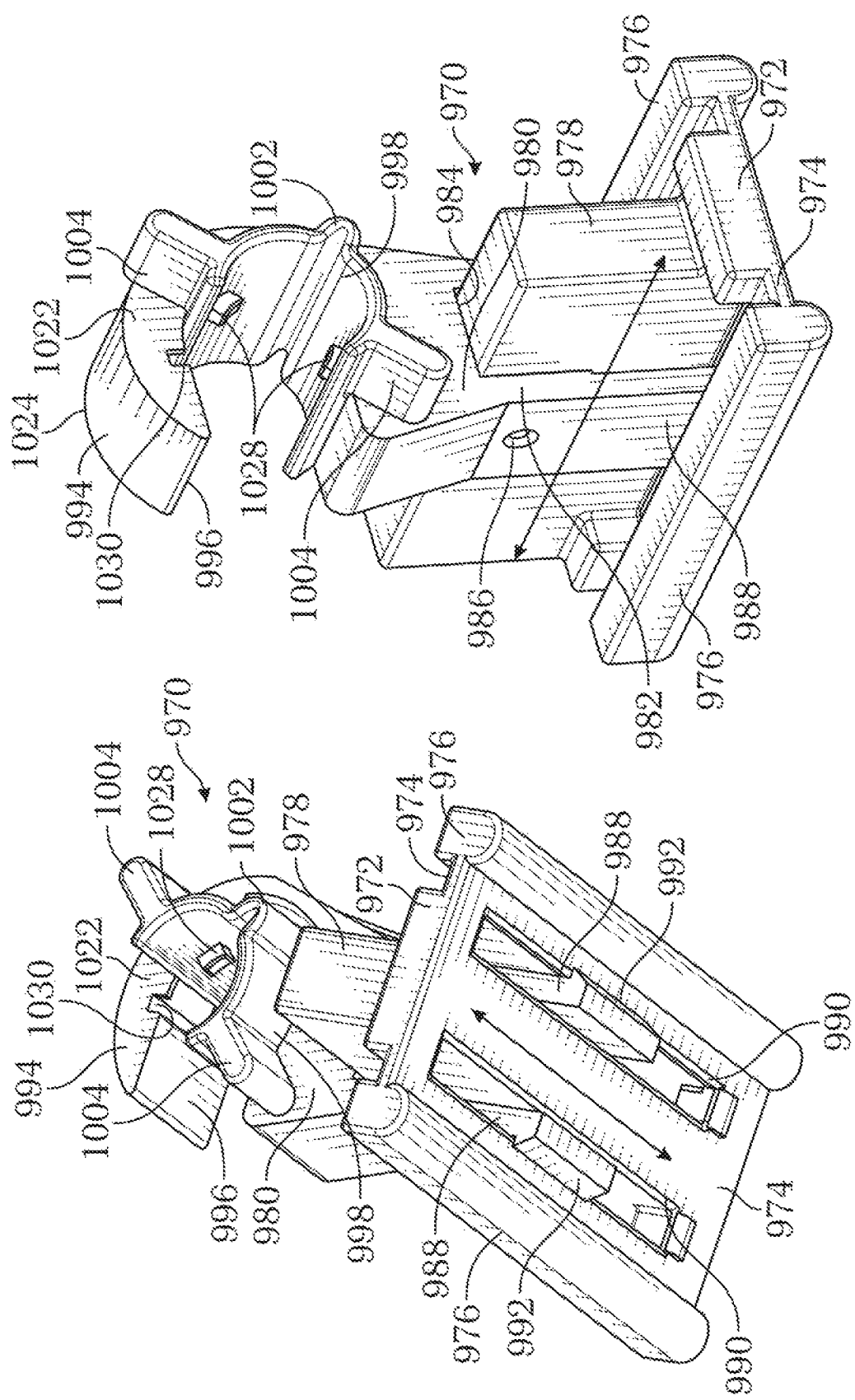

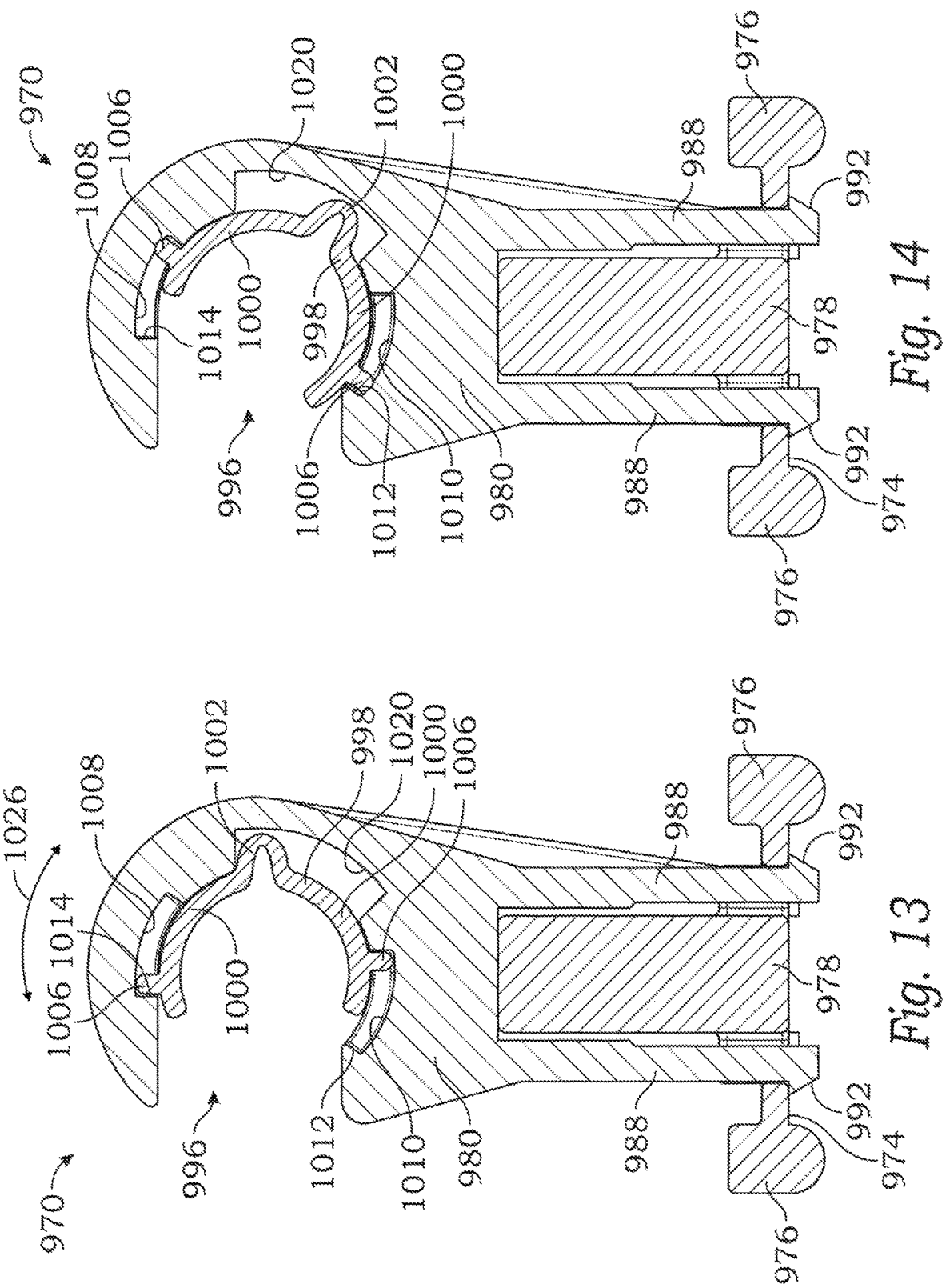

MEDICAL DEVICE STABILIZING APPARATUS AND METHOD OF USE

CROSS-REFERENCE TO RELATED APPLICATIONS

The present application claims the benefit of U.S. Provisional Application No. 62/491,392, filed Apr. 28, 2017, the entire disclosure of which is hereby incorporated herein by reference.

FIELD

The present disclosure relates generally to apparatuses useable to support or stabilize a medical device. Particular implementations relate to stabilizing devices having a passive locking mechanism, or a rotatable locking mechanism, and support tables useable therewith.

BACKGROUND

Prosthetic cardiac valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or death. For many years, the definitive treatment for such disorders was the surgical repair or replacement of the valve during open heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

Balloon-expandable prosthetic valves typically are preferred for replacing calcified native valves because the catheter balloon can apply sufficient expanding force to anchor the frame of the prosthetic valve to the surrounding calcified tissue. On the other hand, self-expanding prosthetic valves sometimes are preferred for replacing a defective, non-stenotic (non-calcified) native valve, although they also can be used to replace stenotic valves.

In addition to valve replacement, transcatheter techniques can be used to repair heart valves. In some cases, repair devices, such as leaflet clips, can be used to improve coaptation of valve leaflets. In other cases, transcatheter techniques can be used to surgically alter a heart valve, such as surgically removing a portion of the native heart valve leaflets to reduce excessive slack.

Because the catheter must be directed through a patient's vasculature, it typically is beneficial for the operator to be able to precisely control the operation of the catheter, including mechanisms that allow the catheter to be bent to assist in navigating the vasculature, and mechanisms that control deployment of the prosthetic valve. During a procedure, the operator can control the catheter using a handle, which can provide controls for extending, retracting, and bending the catheter, including during navigating the patient's vasculature to the delivery or repair site.

Transcatheter procedures can have a long duration, and it may be inconvenient for an operator to manually maintain the position of the catheter handle during the entire procedure. While it may be desirable to adjust the location of the catheter handle relative to the patient at some points during the procedure, at other times it can be desirable to maintain the position of the catheter handle relative to the patient, such as to maintain the depth of insertion of the catheter or the rotational position of the handle.

A catheter handle can be secured to a table proximate the patient using a locking mechanism. Typically, locking mechanisms require a user to actively engage or disengage a locking device to secure or release the catheter handle from a stand or mount. For example, a clamping mechanism may be advanced, such as by advancing a clamp over a threaded shaft, to secure the clamp against the catheter handle and thus secure the catheter handle during a procedure. If it is desired to adjust the position of the catheter handle, the clamp can be released, the position of the catheter handle and/or mount adjusted, and the clamp re-secured. However, these processes can be time consuming and inconvenient.

In addition, some locking mechanisms require a medical device to be inserted through an opening in the locking mechanism that is configured to surround the medical device. It can be cumbersome to insert an axial end of a medical device, particularly a catheter having a long shaft, through the opening, or to remove the device from such a locking mechanism.

SUMMARY

In various aspects, the present disclosure provides a stabilizing apparatus for a medical device, and support tables useable therewith. An embodiment of a stabilizing apparatus comprises a retaining arm. The retaining arm can be slidably or pivotably coupled to a housing. The stabilizing apparatus further comprises a stabilizing fork having a slot configured to receive the medical device. The slot of the stabilizing fork can comprise surface features, such as ridges, to help engage the slot with a handle of the medical device. A biasing member is in contact with the stabilizing fork and configured to urge the stabilizing fork toward the retaining arm. When the medical device is placed in the slot of the stabilizing fork, the biasing member urges the stabilizing fork against an adjacent surface of the medical device, and an opposing surface of the medical device against the retaining arm.

In some aspects, the stabilizing apparatus can be used with a table. For example, the apparatus device can be placed on, and secured to, the table, such as using a clamp. The stabilizing apparatus can comprise arms having recesses configured to be placed under ridges of the table, which can provide a more uniform clamping surface.

In other embodiments, the present disclosure provides a method for stabilizing a medical device. The medical device can be placed within a fork of a stabilizing unit. The fork can be pushed, such as by a medical practitioner, against a biasing force exerted against the fork by a biasing device. A retaining arm of the stabilizing unit can be placed over the medical device. The fork can be released, and the biasing force of the biasing device urges the fork against the medical device and the medical device against the retaining arm. If it is desired to adjust the position of the medical device, the fork can be compressed and released from engagement with the medical device, the medical device repositioned, and the fork released.

In another aspect, the present disclosure provides a method of constructing a platform for use with a medical device. An elongate, generally planar member is folded at a plurality of locations to provide at least one support member and at least one mounting surface. The medical device, such as a stabilizing device described above, is placed on the mounting surface. In particular implementations, the elongate member can be part of packaging used to ship or store a medical device. Segments of the folded elongate member can be coupled to one another, such as using tabs and grooves.

In a further aspect, the present disclosure provides packing useable as a support table. The packaging comprises an elongate, generally planar member adapted to provide a support surface for a medical device, such as a stabilizing device described above. The platform can define a recess for receiving a medical device. The packaging can also comprise at least one support member. At least a portion of the at least one support member can cover the medical device when it is in the recess. At least a portion of the at least one support member can be used to support the support surface when the medical device is removed from the recess.

In a further aspect, the present disclosure provides a stabilizing apparatus having a support member defining a lumen. A rotatable locking member is at least partially disposed in the lumen of the support member. The locking member comprises a lumen and a side opening sized to allow a medical device to be inserted through the opening into the lumen of the locking member. The locking member is rotatable between a first, locked position and a second, unlocked position. When the locking member is in the locked position, the locking member has a first diameter and resists movement of the medical device relative to the locking member. When the locking member is in the unlocked position, the locking member has a second diameter, greater than the first diameter, and permits movement of the medical device relative to the locking member.

The lumen of the support member, in some aspects, can define at least one track. The locking member can include one or more radially outwardly extending protrusions disposed in the track. The track is shaped to push the protrusion radially inwardly as the locking member is rotated to the locked position to radially compress the locking member. In some cases, the track can have an elliptical shape.

The locking member can have an integral spring mechanism to bias the locking member toward the second, unlocked position.

In another aspect, a generally U- or C-shaped support table is provided. The support table can have upper and lower frame members extending laterally from first and second ends of a side frame member. The frame has a side opening opposite the side frame member sized to allow a leg of a patient to be placed within the frame, with the lower frame member extending below the leg and the upper frame member extending above the leg.

There are additional features and advantages of the various embodiments of the present disclosure. They will become evident from the following disclosure.

In this regard, it is to be understood that this is a summary of the various embodiments described herein. Any given embodiment of the present disclosure need not provide all features noted above, nor must it solve all problems or address all issues in the prior art noted above.

BRIEF DESCRIPTION OF THE DRAWINGS

Various embodiments are shown and described in connection with the following drawings in which:

FIG. 3 is an exploded, perspective view of the stabilizing unit of FIG. 1.

FIGS. 5a-5c present perspective views illustrating a process for constructing a support table from medical device packaging.

FIGS. 11 and 12 are perspective views of a distal stabilizing unit of the stabilizing system of FIG. 9.

FIG. 13 is a cross-sectional view of the distal stabilizing unit of the stabilizing system of FIG. 9 in an unlocked configuration.

FIG. 14 is a cross-sectional view of the distal stabilizing unit of the stabilizing system of FIG. 9 in a locked configuration.

DETAILED DESCRIPTION

The present disclosure provides examples of a stabilizing unit for a medical device. The stabilizing unit can comprise a passive locking mechanism, whereby the locking mechanism engages the medical device when not being actively disengaged by a physician. In further aspects, the stabilizing unit includes a rotatable locking mechanism that can be rotated between locked and unlocked configurations. The present disclosure also provides support tables useable with one or more stabilizing units, including support tables constructible from medical device packaging or support tables that can be placed about a portion of a patient.

Figure 1:
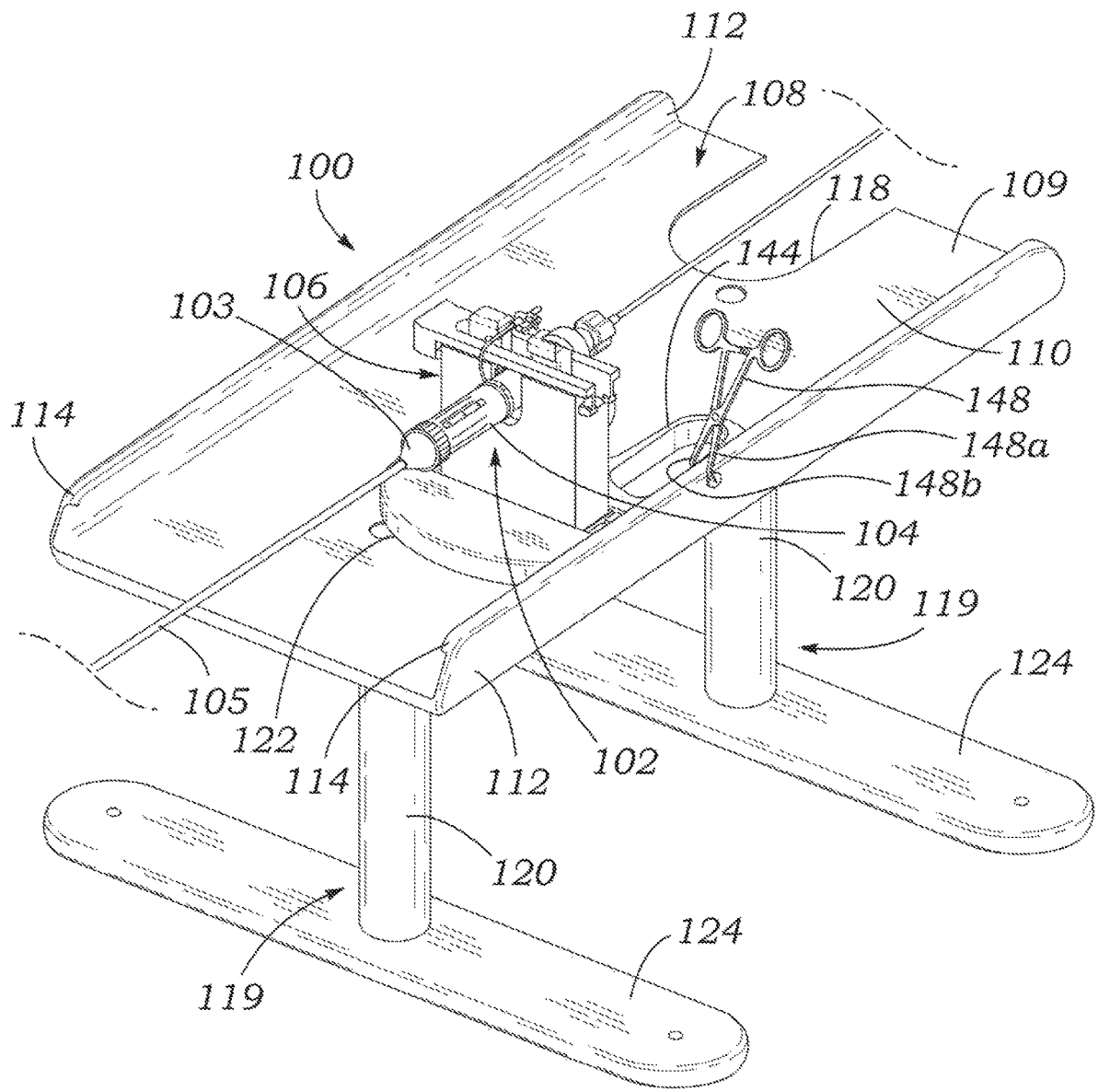
FIG. 1 is a perspective view of a support table and an example embodiment of a stabilizing unit useable with a medical device.

Referring first to FIG. 1, there is shown an example stabilizing system 100 for a medical device 102, such as a transcatheter delivery system comprising a catheter 103 having a handle 104 coupled to an axially extending shaft 105, a distal end of which can be inserted into the vasculature of a patient. The stabilizing system 100 is shown with an example embodiment of a stabilizing unit 106 (also referred to herein as a stabilizing device or a stabilizing apparatus) and a table or platform 108 on which the stabilizing unit can be placed or mounted. The handle 104 of the catheter 103 can be releasably mounted on the stabilizing unit 106.

The catheter 103 can be used for delivering any of various types of implantable medical devices into a patient's body, including, without limitation, prosthetic valves (e.g., prosthetic heart valves), stents, stent-grafts, and various types of leaflet or valve repair devices, such as annuloplasty devices, leaflet clips, and the like. In some implementations, the medical device 102 may comprise an assembly comprised of multiple catheters that are insertable into a patient's body. The handle of each catheter can be mounted on a separate stabilizing unit 106, with all stabilizing units 106 supported on the same platform 108, or on a separate platform.

The table 108 can comprise a generally horizontal portion 109 and a plurality of support members 119. The horizontal portion 109 can define a generally planar mounting surface 110 onto which the stabilizing unit 106 can be placed or mounted. The table 108 can have vertical sides 112 extending upwardly from the longitudinal edges of the horizontal portion 109. The sides 112 can define laterally inwardly extending lips 114 that can define mounting ridges to which the stabilizing unit 106 can be secured, as further described below.

The table 108 can comprise a semi-circular cutout section 118 at a longitudinal end portion of the horizontal portion 109. The cutout section 118 can facilitate operator access to the stabilizing unit 106, including the handle 104 of the catheter 103 secured therein. In other cases, the cutout section 118 can have a different shape, can be located within another portion of the table 108, or can be omitted. Although the table 108 is shown with a rectangular mounting surface 110, the mounting surface can have other shapes, including square, triangular, round, or elliptical shapes.

The plurality of support members 119 can each comprise a vertical component or leg 120 and a horizontal component or foot 124. Each leg 120 can extend downwardly from (such as abutting), and orthogonally to, a lower surface of the horizontal portion 109. The horizontal portion 109 can comprise threaded mounting apertures 122 that receive axially-extending threaded upper end portions (not shown) of the legs 120. A foot 124 can extend laterally from a bottom axial end of each leg 120.

Each leg 120 can comprise an externally threaded lower end portion that threadably engages a mating threaded aperture of its respective foot 124. Alternatively, the feet 124 can comprise axially extending threaded posts that extend into internally threaded apertures in the bottom axial ends of the legs 120. In yet further implementations, the feet 124 and the legs 120 can be securely coupled in another manner, such as by welding or the use of a suitable adhesive, fasteners (e.g., screws), or the support members 119 can be of unitary construction (e.g., the legs 120 and feet 124 molded as a unit). The feet 124 can be dimensioned and shaped such that they can be placed on a surface, such as an operating table, to provide resistance against tipping or torsional movement of the table 108, thus maintaining the mounting surface 110 in an at least substantially horizontal position.

In particular examples, components of the table 108 can be dimensioned and positioned with respect to one another such that the table may be placed between the legs of a patient lying on an operating table. For example, the legs 120 can be placed between the patient's legs, with the feet 124 resting on an operating table. The patient's legs can be placed over the feet 124 to help maintain the table 108 in a desired position, including resisting translational and torsional movement. The feet 124 can dimensions, including width and thickness, that is sufficiently small such that placing the legs of the patient over the feet does not cause the patient discomfort. The feet 124 can have a length sufficiently long to extend underneath the legs of a patient such that the patient's legs can rest on top of the feet and help secure the table 108 in place relative to the patient during a procedure. If desired, the table 108 can be further anchored in place against the patient and/or the operating table, such as by using fasteners, adhesive tape, sutures, or other fastening means.

Figure 2:
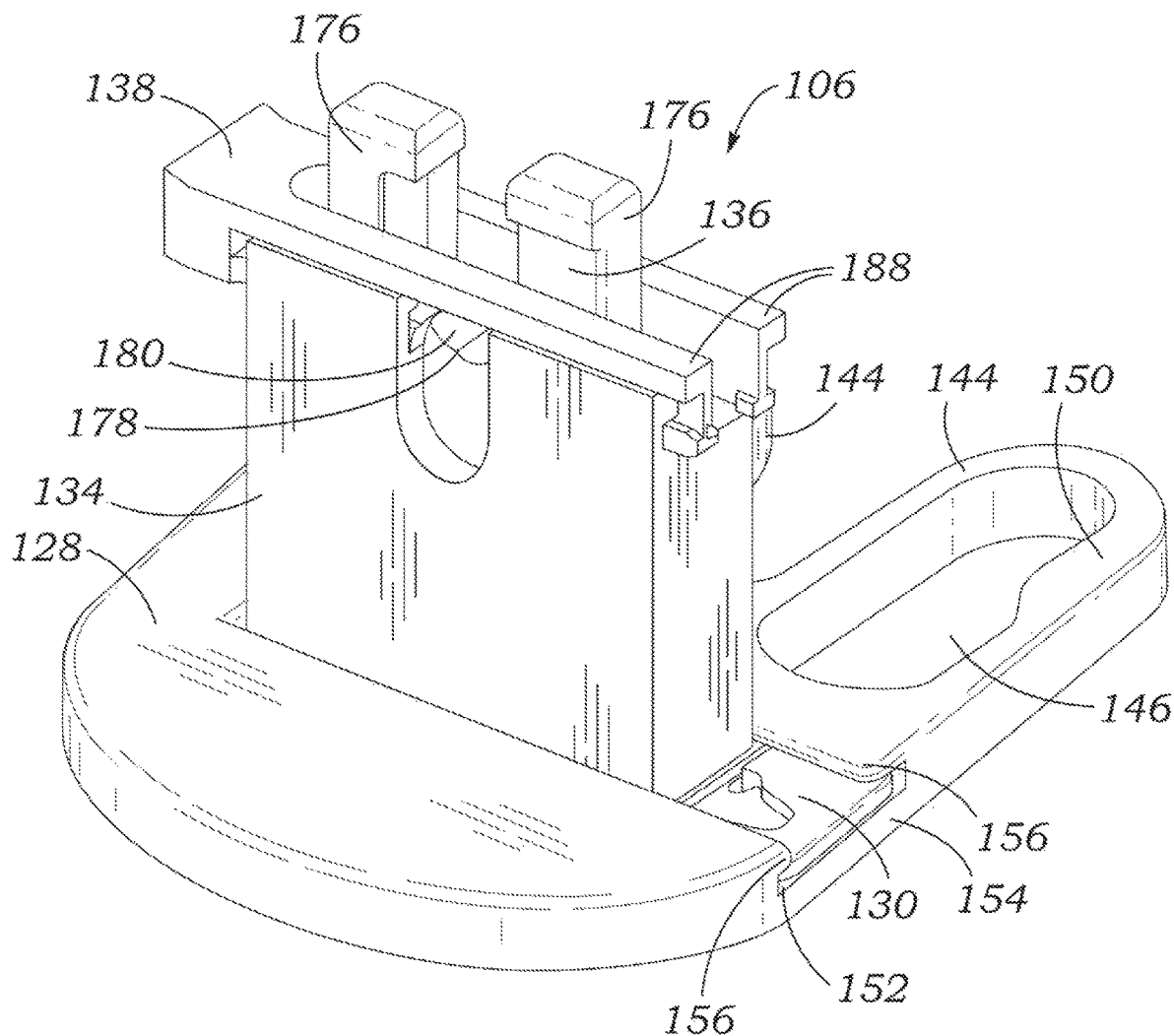
FIG. 2 is a perspective view the stabilizing unit of FIG. 1.

With reference to FIGS. 2 and 3, the stabilizing unit 106 can comprise a base member 128, a lower housing portion 130, an upper housing portion 134, a stabilizing fork 136, and a retaining arm 138. The handle 104 of the medical device 102 can be secured by a yoke formed from semicircular or U-shaped slots 140, formed in the stabilizing fork 136, and slots 196, formed in the retaining arm 138.

The base member 128 can comprise a broad, U-shaped body comprising a plurality of longitudinally extending arms 144, and a laterally extending slot 152. The body of the base member 128 can have an at least substantially planar bottom surface adapted to be mounted on the mounting surface 110 of the table 108. The arms 144 can comprise longitudinally extending cutout sections 146. In at least some cases, the cutout sections 146 can extend through the upper and lower surfaces of the arms 144 (i.e., the cutout sections extend the entire height of the arms 144). In other cases, a portion of the bottom of the base 128 can extend beneath the cutout sections 146, such that the cutout sections 146 do not extend through the bottom surfaces of the arms 144 (i.e., the cutout sections are recessed portions in the upper surfaces of the arms 144). The cutout sections 146 can be used to help secure the base member 128 to the table 108.

For example, as shown in FIG. 1, a clamp 148 can be used to secure an arm 144 to a vertical side 112 of the table 108. The width of the exterior, longitudinally extending side 150 (FIG. 2) of the arm 144 can be selected to be at least about the same as the width of the lips 114 (FIG. 1). Thus, when placed against a lateral side 112 of the table 108, the inner edge of the side 150 of the arm 144 can be at least substantially flush with the mounting ridge provided by the adjacent lip 114, which can facilitate clamping or otherwise securing the stabilizing unit 106 to the table 108. As shown in FIG. 1, one clamping arm or member 148a of the clamp 148 can be placed against the outer surface of the adjacent lateral side 112, and the other clamping arm or member 148b of the clamp can be placed against the inner surface of side 150 within the cutout section 146.

In other embodiments, rather than using a separate clamp 148, the stabilizing unit 106 can incorporate a clamping mechanism. For instance, an outer, lateral surface of an arm 144 can incorporate a clamp that can be secured to a lateral side 112 of the table 108. In yet further embodiments, a clamp need not be used with the stabilizing unit 106. If desired, a bottom surface of the stabilizing unit 106 can be formed from a material with a large coefficient of friction, or pads of a material with a large coefficient of friction can be attached (such as being adhered) to a bottom surface of the stabilizing unit. The stabilizing unit 106 can be constructed from a material having a weight sufficient to help retain the stabilizing unit at a desired position on the table 108.

As best shown in FIG. 3, the laterally extending slot 152 can extend from one side 154 of the base member 128. The slot 152 can have a reduced width proximate the top of the base member 128, defining longitudinally extending ridges 156. The lower housing portion 130 can be disposed within the slot 152. The lower housing portion 130 can have a width greater than the gap between the ridges 156. Thus, when inserted into the slot 152 through the side 154 of the base member 128, the lower housing portion 130 can be secured against upward movement relative to the base member and against movement perpendicular to the length of the slot 152.

The lower housing portion 130 can comprise a lower portion 158, an upper mounting section 166, and a plurality of vertical post members 168. As best shown in FIG. 3, the lower portion 158 can comprise a plurality of apertures 160 that extend from the upper surface of the lower portion 158 through a bottom surface of the lower portion 158. Each of the apertures 160 can receive a fastener 162, such as the illustrated screw. The fasteners 162 can be received by threaded apertures (not shown) of the upper housing portion 134. The fasteners 162 can thus secure the lower housing portion 130 and upper housing portion 134 to one another.

As further shown in FIG. 3, the mounting section 166 can extend upwardly from the upper surface of the lower portion 158, and can have an obround horizontal cross sectional shape, although other shapes can be used (e.g., rectangular). The post members 168 can extend upwardly from the mounting section 166, such that the longitudinal axes of the post members are orthogonal to the upper surface of the mounting section. Each post 168 can be configured and dimensioned to receive a biasing member 170, such as the illustrated coil spring. Each post 168 can extend coaxially through the lower end portion of a respective biasing member 170. Each post 168 can be encircled by a well or recessed portion 172 formed in the upper surface of the mounting section 166 and configured to receive a lower end portion of a respective biasing member 170. The wells 172 can assist in maintaining the position of their respective biasing members 170 relative to a respective post member 168 and the mounting section 166. The upper end portion of each biasing member 170 can extend through a respective aperture (not shown) formed in a bottom surface of the stabilizing fork 136 and can bear against an inner surface within the stabilizing fork 136. In this manner, the biasing members 170 apply a biasing force that biases the stabilizing fork 136 away from the lower housing portion 130.

The stabilizing fork 136 can comprise an enlarged lower portion 174 dimensioned to fit over the mounting section 166 of the lower housing portion 130. For example, the lower portion 174 can extend around the mounting section 166, abutting the upper surface of the lower portion 158 of the lower housing, when the stabilizing fork 136 is depressed downwardly by a user wishing to adjust the position of a medical device secured thereby, as further described below. In at least some aspects, the height of the mounting section 166 and the height of the lower portion 174 can be selected based on the desired degree of travel of the stabilizing fork 136 between its compressed and released positions. That is, the heights can correspond to the degree of travel of the stabilizing fork.

The stabilizing fork 136 can comprise arms 176 separated by the U-shaped slot 140. The base of the slot 140 can comprise a plurality of ridges 178 extending transversely between the vertical faces of the stabilizing fork 136. The ridges 178 can define scalloped mounting recesses 180 that can be configured to engage surface features of a medical device, such as the handle 104 of the catheter 103, to help secure the handle against rotational movement relative to the stabilizing fork 136.

The upper housing portion 134 can comprise longitudinally extending U-shaped slots 142 formed in the vertical side walls 183 of the upper housing portion and a laterally extending inverted T-shaped slot 184 formed in the upper end portion of the upper housing portion. The U-shaped slots 142 can have at least approximately the same width as the U-shaped slot 140 of the stabilizing fork 136. The inverted T-shaped slot 184 can have an upper portion 192 (the stem of the T) having a width smaller than the width of a lower portion 191 (the crossbar of the T). The side walls 183, the sides of the slot 184, and the upper ends 182 of the upper housing portion 134, can be spaced apart to provide a vertical aperture 186 between the faces through which the arms 176 of the stabilizing fork 136 can extend.

The retaining arm 138 can comprise guide rails 188, the slot 196, and a stop 198. The slot 184 can be configured to receive lower portions 194 of the guide rails 188 of the retaining arm 138. The lower portions 194 are configured to extend into recesses of the slot 194 formed by the lower portion 191 of the slot 184. Upper portions 195 of the guide rails 188 are configured to abut the upper ends 182 of the upper housing portion 134. The upper 195 and lower 194 portions of the guide rails 182 can have a larger width than an intermediate portion of the guiderails, forming an outwardly facing groove 197.

The guide rails 188 can be spaced apart to provide an aperture 190 through which the upper end portions of the arms 176 of the stabilizing fork 136 can extend. The upper portion 192 of the slot 184 can have a smaller width than the lower potion 194 and upper portion 195 of the guide rails 188, thus preventing the guide rails from being removed from the slot by moving them upwardly, away from the upper housing portion 134. That is, the groove 197 can be slid over the upper portion 192 of the slot 184.

The stop 198 can extend downwardly from a bottom surface of the retaining arm 138. The stop 198 can be configured to engage a lateral side of the upper housing portion 134, limiting movement of the retaining arm 138 relative to the upper housing portion.

The guide rails 188 can define the semi-circular (or, in some cases, U-shaped) slots 196. The slots 196 can comprise ridges 178 and mounting recesses 180 like the slot 140 of the stabilizing fork 136. The slots 196 of the retaining arm 138 can cooperate with the slots 142 of the upper housing portion 134 and the slot 140 of the stabilizing fork 136 to form a yoke useable to secure a medical device placed therethrough.

In use, the support members 119 (FIG. 1) can be placed on an operating table, with the legs 120 between a patient's legs. The patient's legs can be placed over the feet 124 to help secure the table 108. The stabilizing unit 106 can be placed on the support surface 110 of the table 108. The stabilizing unit 106 can be moved to a desired longitudinal position on the support surface 110 and moved laterally to abut a lateral side 112 of the table 108. The stabilizing unit 106 may then be secured in position, such as by attaching the clamp 148 about the side 150 of the outer arm 144 of the base 128 and the outer surface of the lateral side 112. The side 150 of the arm 144 can be positioned beneath the lip 114 such that the inner edge of the recess 146 and the outer edge of the lip are flush, which can help provide a uniform clamping surface for the clamp 148. Although one clamp 148 is shown in FIG. 1, in practice, multiple clamps can be used, or the stabilizing unit 106 secured to the table 108 by other means.

With reference to FIGS. 2 and 3, the retaining arm 138 of the stabilizing unit 106 can be removed from the stabilizing unit, or retracted from the slot 184 of the upper housing portion 134 so as to allow the handle 104 of the catheter 103 to be placed in the slots 140 and 142. While the handle 104 is being placed in the slots 140 and 142, the stabilizing fork 136 can be manually depressed toward the lower housing portion 130 against the biasing force of the biasing members 170 to move the slot 140 lower relative to upper housing portion 134.

With the handle 104 inserted within the slots 140 and 142, the retaining arm 138 can be slid toward the upper housing portion 134 to place the slots 196 over the slots 140 and 142. Manual pressure on the stabilizing fork 136 can then be released, which allows the biasing members 170 to push the lower surface of the slot 140 against a lower circumferential surface of the handle 104 of the catheter 103 and an upper circumferential surface of the handle 104 against the slots 196. The upwardly directed force of the biasing members 170 holds the handle 104 of the catheter 103 between the stabilizing fork 136 and the stabilizing arm 138 and resists against inadvertent axial and rotational movement of the catheter 103 relative to the stabilizing unit. The ridges 178 and mounting recesses 180 can mate with corresponding features on the handle 104 to help secure the handle against rotational movement within the slots 140 and 196.

If an operator desires to adjust the position of the medical device 102 (the axial and/or rotation position of the medical device), the operator can manually depress the stabilizing fork 136 to move the slot 140 out of engagement with the handle 104. While maintaining the compressive force against the stabilizing fork 136, the operator can adjust the position of the catheter handle 104, including rotating it or moving it distally or proximally relative to a patient. When the operator is satisfied with the position of the medical device 102, the operator can remove the compressive force from the stabilizing fork 136, whereby the biasing members 170 will again urge the stabilizing fork 136 upwardly such that the slot 140 abuts the handle 104, securing the handle between the slot 140 and the slots 196 of the retaining arm 138. The operator can repeat this adjustment as desired during a medical procedure.

Although one stabilizing unit 106 is shown placed on the table 108, plural stabilizing units 106 can be placed on the same table 108 and used to secure respective medical devices during a medical procedure. For example, if the medical assembly includes multiple catheters inserted coaxially through one another, the stabilizing units 106 can be placed one behind the other along the length of the platform 108, with the handle of each catheter mounted in one of the stabilizing units. In another example, if the medical assembly includes multiple catheters placed side-by-side, the stabilizing units 106 can be placed side-by-side or laterally spaced across with the width of the platform 108, with the handle of each catheter mounted in one of the stabilizing units.

Figure 4:
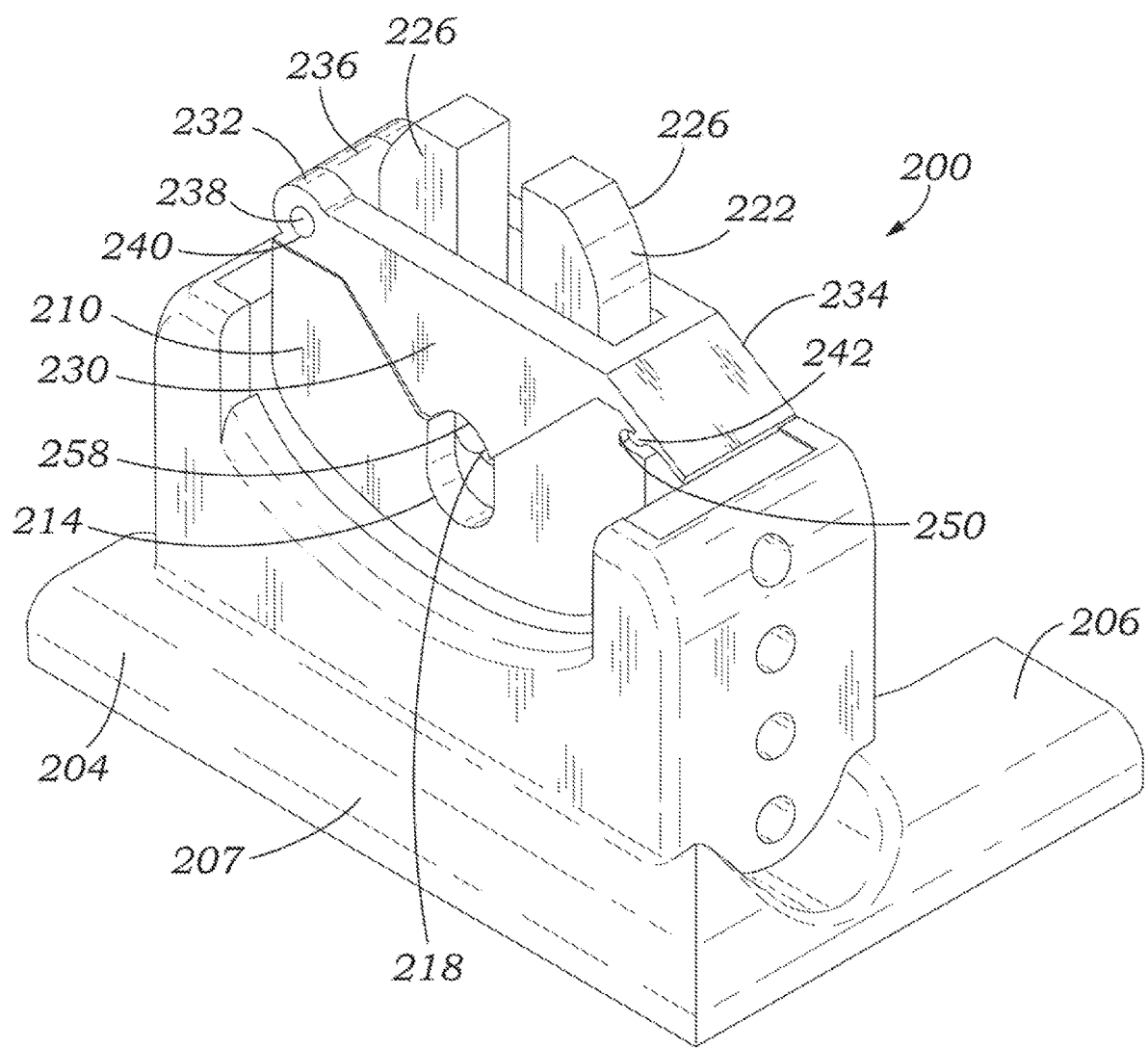
FIG. 4 is a perspective view of another example embodiment of a stabilizing unit useable with a medical device.

FIG. 4 illustrates another example of a stabilizing unit 200 that can be used with the medical device 102 and the table 108 of FIG. 1. The stabilizing unit 200 can comprise a base member 204, a housing 210, a stabilizing fork 222, and a pivotable retaining arm 230. The base member 204 can have arms 206 (one of which is visible in FIG. 4) extending rearwardly from an elongate portion 207 of the base member. Although not shown in FIG. 4, in some cases, the arms 206 can comprise cutout sections, analogous to the cutout sections 146 of the arms 144 of the base member 128 of FIG. 2. The cutout sections can be used to help secure the stabilizing unit 200 during a medical procedure, such as by clamping the stabilizing unit to a support table.

The housing 210 can define vertical, U-shaped slots 214 formed in the front and rear vertical side walls of the housing. The U-shaped slots 214 can be aligned with a U-shaped slot 218 formed in the stabilizing fork 222. The U-shaped slot 218 can define vertically extending arms 226 of the stabilizing fork 222, which can extend upwardly through the retaining arm 230. The stabilizing fork 222 can be mounted in a space between the opposing front and rear vertical side walls of the housing 210.

The pivotable retaining arm 230 can comprise a mounting end portion 232 and an actuating tab 234. The mounting end portion 232 can be hingeably connected to a mounting projection 236 extending vertically from a lateral side of the upper end of the housing 210. For example, the mounting end portion 232 can be connected to the mounting projection 236 using a pin 238 or similar coupling mechanism inserted through apertures 240 formed in the mounting end portion 232 (one of which is shown in FIG. 4) and a mating aperture formed in the mounting projection 236 (not visible in FIG. 4).

The actuating tab 234 can define a tongue 242 inwardly extending toward the lower end of the housing 210 from a lower surface of the actuating tab. The upper end portion of the housing 210 can define a groove 250 for receiving the tongue 242, allowing the retaining arm 230 to be releasably secured to the housing 210.

The lower longitudinal surface of the retaining arm 230 can define semi-circular (or, in some cases, U-shaped) slots 258. The slots 258 of the retaining arm 230, the slots 214 of the housing 210, and the slot 218 of the stabilizing fork 222 can cooperate to form a yoke that can abut a medical device extending therethrough. The stabilizing fork 222 can be biased towards the retaining arm 230, such as using springs or other biasing members, which can be placed in contact with the stabilizing fork in a similar manner as the biasing devices 170 and the stabilizing fork 136 of FIGS. 2 and 3.

The stabilizing unit 200 can be used in a similar manner as the stabilizing unit 106. When a medical device is to be inserted into the stabilizing unit 200, the tongue 242 can be removed from the groove 250 by pulling the actuating tab 234 and pivoting the retaining arm 230 away from the housing 210. The stabilizing fork 222 can be manually depressed, and the medical device can be inserted within the slots 214, 218. The retaining arm 230 can then be pivoted toward the housing 210 and the tongue 242 secured within the groove 250. The compressive force on the stabilizing fork 222 can be removed, allowing the stabilizing fork to move upwardly towards the retaining arm 230, and urging the slot 218 against the lower surface of the medical device, and in turn pushing the medical device against the bottom of the slots 258. The position of the medical device can be adjusted by again manually depressing the stabilizing fork 222 such that the slot 218 is moved out of engagement with the medical device.

Components of a stabilizing system, such as the medical device 102, the stabilizing unit 106 (or the unit 200), and the table 108, are typically shipped to a location (such as a clinic or hospital) where a medical procedure is to be performed. In at least some cases, the packaging used to ship or store system components can be used to construct all or a portion of other system components. In particular, packaging can be used to construct all of a portion of a table on which a stabilizing unit can be placed.

FIGS. 5a-5c illustrate a packaging sheet 300 in which a medical device, such as an introducer sheath or a guide sheath, can be shipped to a location (such as being shipped within a box, carton, or other type of packaging). The packaging sheet 300 can comprise a recess 308 for receiving a handle 304 the medical device, a plurality of support members 312, and a plurality of retaining members 324, such as brackets or straps. The packaging sheet can be constructed from a sterilizable, suitably rigid material, such as polycarbonate or high density polyethylene (HDPE). The recess 308 can be configured and dimensioned to hold the medical device 304 and protect it from damage during transit.

The support members 312 can be pivotable relative to the sheet 300 and can each have an upper leg 320 and a lower leg 326 connected to each other by a connecting post 322. The upper leg 320 of each support member 312 can be secured to a bottom surface 316 of the packing sheet 300 by the retaining members 324, which can be secured to the bottom surface of the packaging sheet, such as with a suitable adhesive, by welding, and/or fasteners. Although not shown, in a shipping and storage configuration 328, the lower leg 326 of one or both of the support members 312 can be disposed over a portion of the recess 308, thus helping secure the handle 304 of the medical device within the recess and protecting it from damage.

With reference to a use configuration 332, when the medical device 304 is to be used, or the packaging sheet 300 is otherwise desired to be converted to a table for use in a medical procedure, the support members 312 can be pivoted by rotating the lower legs 326 outwardly such that the support members 312 extend vertically from the bottom surface 316 of the packaging sheet 300.

The packaging sheet 300 can be turned over and the lower legs 326 placed on a supportive surface, such as an operating table (not shown) to provide an unfolded and operative configuration 340, as shown in FIG. 5c. One or more stabilizing units 344a, 344b, such as the stabilizing unit 106 of FIG. 1 or the stabilizing unit 200 of FIG. 4, can be placed on an upper surface 348 of the packaging sheet 300. The upper surface 348 can provide a support surface for the stabilizing units 344a, 344b. Medical devices 350a, 350b (which can include the handle 304) can be mounted on the stabilizing units 344a, 344b.

Figure 6:
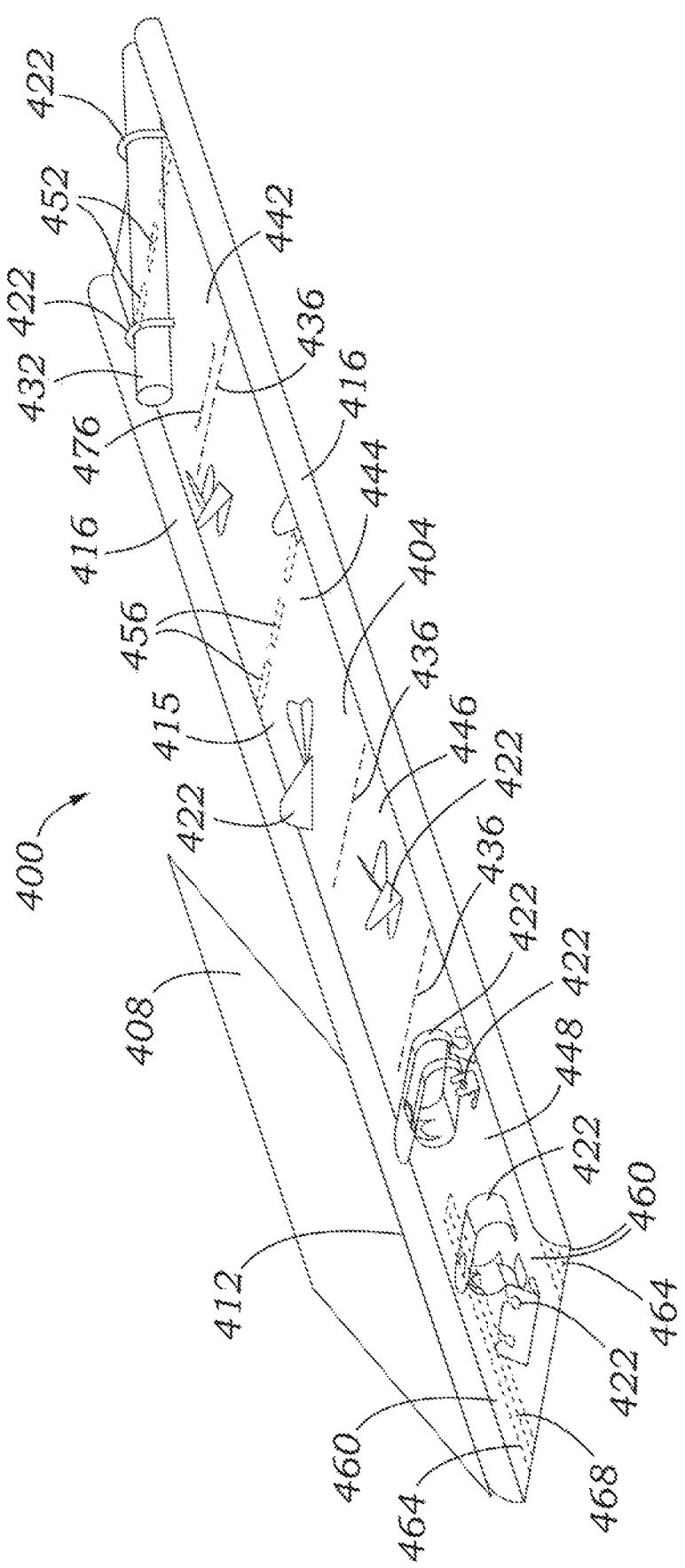
FIG. 6 is a perspective view of medical device packaging that can be used to construct a support table for a medical device.
Figure 7:
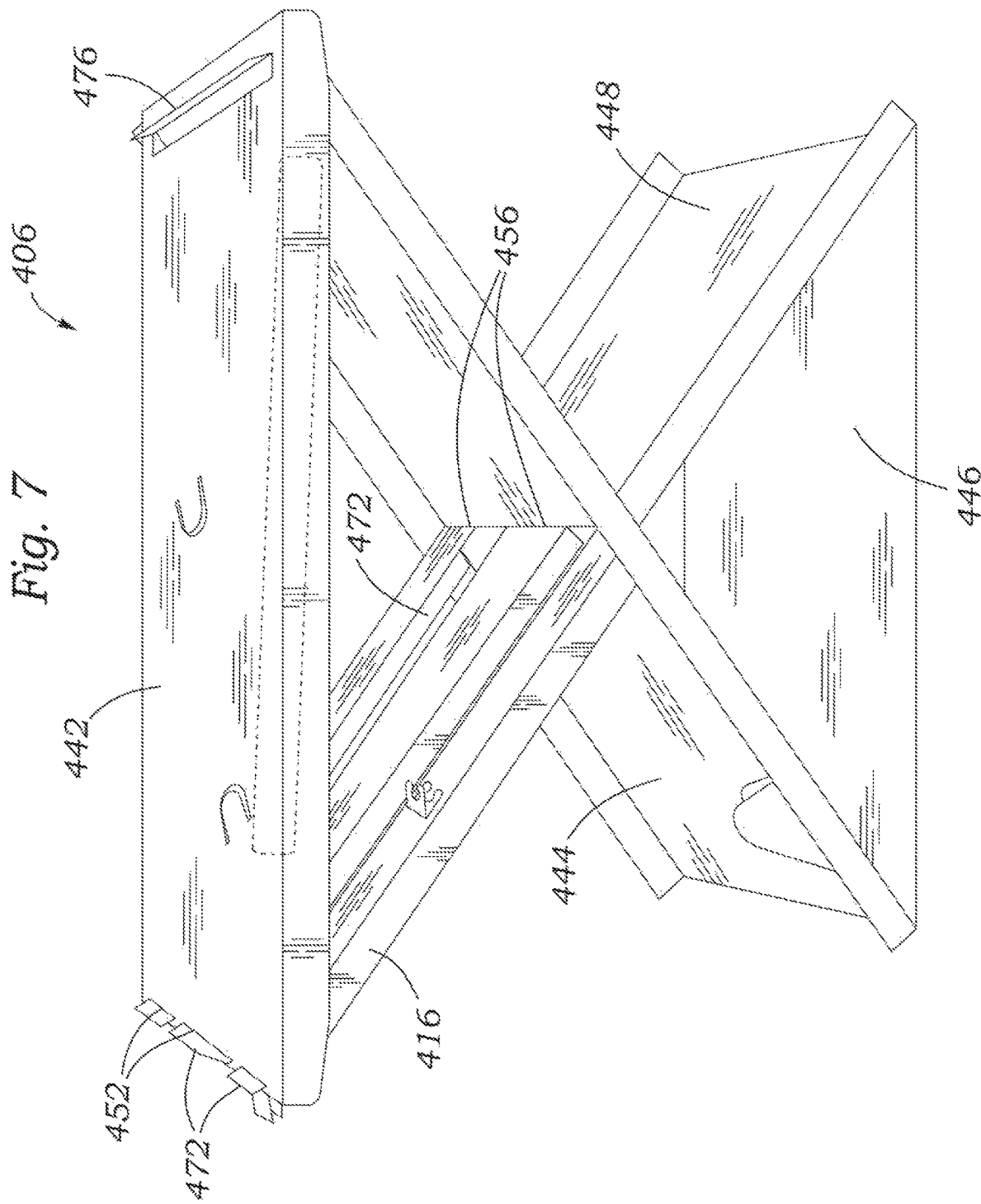
FIG. 7 is a perspective view of a support table formable from the packaging of FIG. 6.

FIG. 6 illustrates another example of a packaging sheet 400 that can be used to construct all or a portion of a table or platform 406, shown in FIG. 7, on which a stabilizing unit (e.g., the stabilizing unit 106 or the stabilizing unit 200) can be placed. The packaging sheet 400 can comprise a base 404, a flap 408, longitudinal ridges 416, a plurality of retaining members 422, a plurality of fold points 436, slots 452, 456, and tabs 460. Like the packaging sheet 300, the packaging sheet 400 can be constructed from a sterilizable, suitably rigid material, such as polycarbonate or high density polyethylene (HDPE). The base 404 can be elongate, generally planar, and generally rectangular.

The flap 408, which can be generally rectangular, can extend from the side of a longitudinal end portion of the base 404. The flap 408 can be used, for example, to help protect components (such as a prosthetic valve, a delivery assembly for a prosthetic valve, a stabilizing unit, or components thereof) from damage during transit. In some cases, the flap 408 can be removed prior to constructing the table 406 from the packaging sheet 400. The flap 408 can be cut or torn off, for example, and the flap can comprise features to assist in its removal. A side 412 of the flap 408 extending from the base 404 can comprise perforations, scoring, or creases to assist in removing the flap from the base. In other cases, the flap 408 can be folded behind the base 404 and used to help provide structural support to the table 406, such as by making a span of the table 406 more rigid.

The longitudinal ridges 416 can extend vertically from, and orthogonally to, a horizontal portion 415 of the base 404. The ridges 416 can be formed by folding the sides of the base 404. The base 404 can comprise creases or other features to aid in forming the ridges 416. In other cases, the packaging sheet 400 can comprise preformed ridges 416, such as being molded to comprise both the horizontal portion 415 and the ridges.

The retaining members 422, such as flaps, loops, straps, and notches, can be formed from, or coupled to, the base 404. The retaining members 422 can be used to help secure and organize components of a prosthetic valve, delivery assembly, or stabilizing unit during transit. For instance, retaining members 422 (e.g. loops) can be used to secure a tube 432. The tube 432 can be used to house a prosthetic valve within a storage tube (not shown). Other retaining members 422 (e.g., straps and notches) can be used to secure components of a delivery assembly, such as a guide sheath (e.g., the guide sheath 304 of FIG. 5) and tubes and shafts extending therefrom.

The base 404 can be folded at the fold points 436, which can extend laterally across the base, to construct the table 406. The fold points 436 can be creased, scored, or perforated to assist a user in identifying the correct fold location, folding the base 404 in the correct direction, and allowing the base to fold more easily about a fold point. In the illustrated embodiment, the base 404 comprises three fold points 436. The fold points 436 can divide the base into a plurality of segments 442, 444, 446, and 448. Depending on how the table 406 is constructed, more or fewer fold points 436 can be included or used. For example, the base 404 can produce a U-shaped table using two fold points.

In some configurations of a table 406, one of the segments 442, 444, 446, 448 may need to pass through, or be secured to, another segment. For example, with additional reference to FIG. 7, an end portion of segment 448 can be configured to be inserted through the slots 452, formed in an end portion of segment 442, and the slots 456, formed in a midsection of segment 444. Returning to FIG. 6, in some cases, the slots 452, 456 can be pre-formed (such as precut) in the segments 442, 444. In other cases, the slots 452, 456 can be formed by cutting or otherwise removing material from the segments 442, 444 during assembly of the table 406. For instance, the segments 442, 444 can comprise scored or perforated lines defining the slots 452, 456. During table assembly, a user can punch out the perforated or scored material to produce the slots 452, 456.

As shown best in FIG. 6, segment 448 can comprise the tabs 460, which can be inserted into mating slots 452, 456. The tabs 460 can be formed by folding the material of the segment 448 or by removing material from the segment. As shown, each tab 460 can comprise longitudinally extending fold lines 464. A longitudinal slit 468 can be formed between the fold lines 464. For example, the slit 468 can be cut by a user, or can be pre-formed in the segment 448 (such as by precutting the slit, or including perforations or scoring to assist a user in forming the slit). When the table 406 is assembled, the lateral sides of the tabs 460 can be folded about the longitudinal axis of the base 404, and the tabs thereby formed can be inserted through the slots 452, 456. After being inserted through the slots 452, 456, the material of the segment 448 folded about the tabs 460 can be unfolded, with the widened portions 472 (FIG. 7) helping to prevent the tabs from slipping back through the slots.

In another aspect, rather than folding the segment 446 to produce the tabs 460, strips of material (e.g., the material between the fold lines 464) can be removed from the segment 448 to form the tabs. In order to facilitate the removal of the strips of material, the fold lines 464 can be scored or perforated.

The segment 442 can define a flap 476. The sides of the flap 476 can be creased, scored, or perforated to help a user fold the flap out (e.g., by rotating the flap about a lateral axis of the base 404) during table assembly. The flap 476 can be used to help secure a stabilizing unit to the table 406 during a medical procedure.

FIG. 7 illustrates the table 406 in its assembled form. Segment 444 has been folded at least approximately 135 degrees clockwise, beneath segment 442. Segment 446 has been folded at least approximately 135 degrees clockwise, beneath segment 444, such that segment 446 is disposed below, and parallel to, segment 442. The ridges 416 of segment 446 can be folded over or underneath (e.g., about the longitudinal axis of segment 446) the segment. Segment 448 has been folded at least approximately 135 degrees clockwise, above segment 446.

Segment 448 can intersect segment 444 at least approximately at the longitudinal midpoint of segment 444. The tabs 460 of segment 448 are shown inserted through the slots 456 of segment 444 and the slots 452 of segment 442. The ridges 416 are shown as downwardly folded after passing upwardly through the slots 456. The downwardly folded ridges 416 can provide widened portions 472 that can help prevent the tabs 460 from sliding back through the slots 456, helping to make the table 406 more rigid and secure. Similarly, the widened portions 472 proximate the slots 452 can help prevent the tabs 460 from sliding back through the slots.

The flap 476 is shown as extending upwardly from the surface of the segment 442. A stabilizing unit can be placed on the surface of the segment 442, which provides a support surface, and secured to the flap 476. For example, a stabilizing unit can be secured to the flap 476, in an analogous manner to how the stabilizing unit 106 of FIG. 1 is secured to the lip 114 of the table 108 using the clamp 148. Segment 446 can provide a support member of the table 406.

The use of packaging to produce tables or platforms for a medical device (such as a stabilizing unit) can provide a number of advantages. For instance, it can be less wasteful of material, and less expensive, than providing a table as a separate, discrete component. In addition, the table, at least in part because of its inexpensiveness, can be a single-use, disposable component. Although a single table is shown, packaging can be provided to provide multiple tables, one or more of which can be used in a medical procedure.

Figure 8:
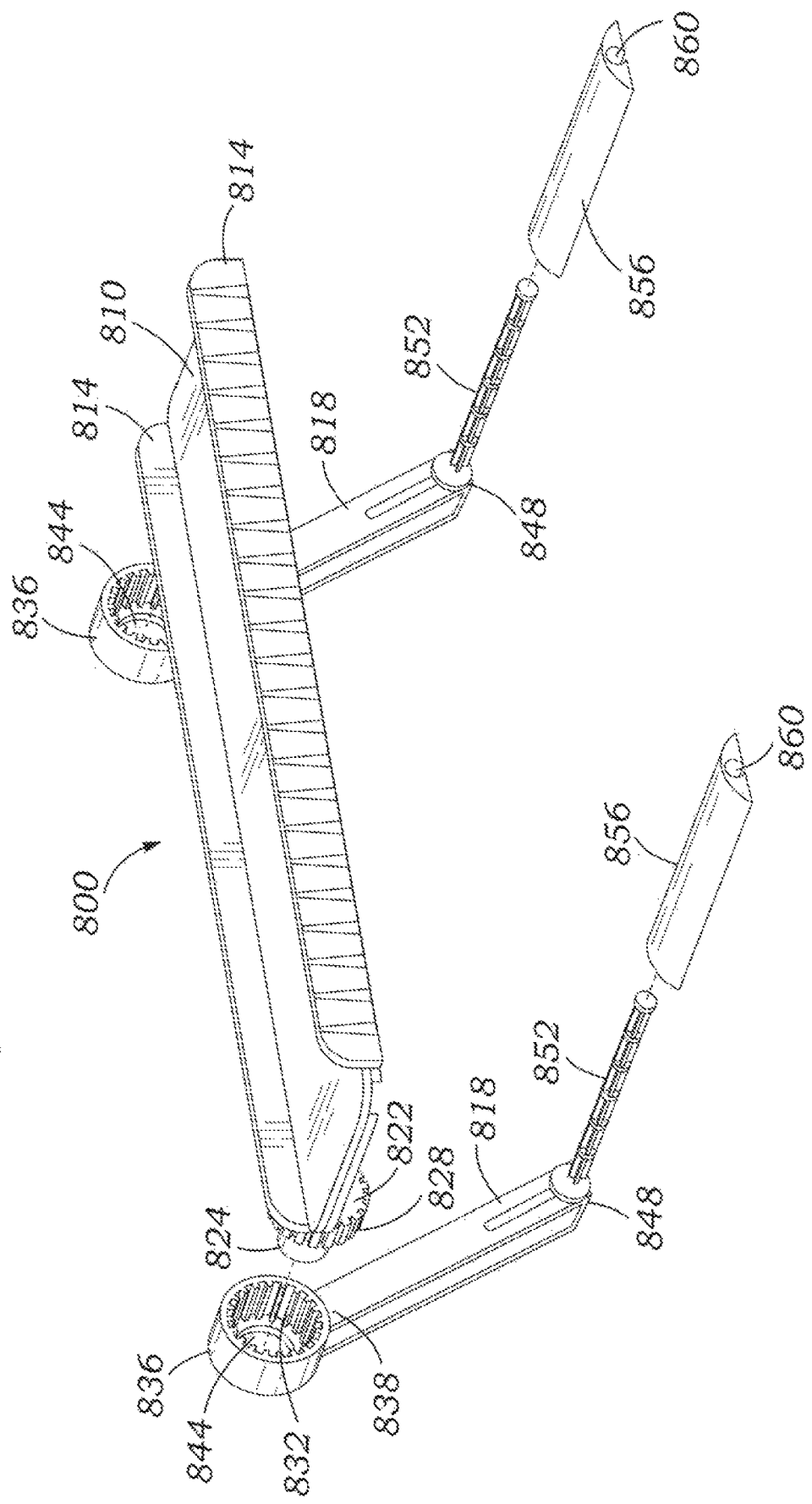
FIG. 8 is a perspective view of another example embodiment of a support table that can be used with a medical device or a stabilizing unit therefor.

FIG. 8 illustrates another example embodiment of a table 800 that can be used with a medical device or a support therefor, including the stabilizing unit 106 of FIG. 1 or the stabilizing unit 200 of FIG. 4. The table 800 has an elongate surface 810, two lateral sides 814, extending vertically from the elongate surface, and a plurality of support members, or legs, 818. If desired, the lateral sides 814 can incorporate a lip, which can be analogous to the lip 114 of the table 108 of FIG. 1. Although the elongate surface 810 and lateral sides 814 are shown as unitary, contiguous surfaces, the elongate surface, lateral sides, or both, may be constructed from multiple pieces which can be secured together. For instance, the elongate surface 810 can be formed from two, or more, hingeably coupled pieces, or multiple pieces can be joined in a snap-fit fashion.

The table 800 can include a plurality of coupling members 822 (one of which is visible in FIG. 8). The coupling members 822 can extend laterally from one or both of the lateral sides 814 of the table 800, and can be integrally formed with the lateral sides, or coupled to the lateral sides, such as by welding, adhesion, or the like. The coupling members 822 can include a cylinder or rod 824 that extends laterally, axially outwardly from a toothed ring 828. The teeth of the toothed ring 828 can be configured to matingly engage teeth 832 formed on a radial internal surface of an annular receptacle 836 disposed at an upper end 838 of each support member 818. The receptacles 836 can have an inner dimension selected to receive the toothed ring 828, and can include an axial opening 844 dimensioned to receive the cylinder 824 of a coupling member 822.

In some implementations, the receptacles 836 can be selectively detached from the coupling members 822, and the coupling members can be maintained at a fixed position with respect to the lateral sides 814 (e.g., the coupling members do not rotate), or the coupling members can be maintainable at a fixed position (e.g., they can be locked at a desired position). Thus, the height and angle of the elongate surface 810 of the table 800 can be adjusted by manipulating the position of the support members 818 relative to the lateral surface, and then inserting the receptacles 836 over their respective coupling member 822 when the lateral surface is at a desired position. The height of the elongate surface 810 can be adjusted, but maintained in a horizontal position, by rotating the support members 818 relative to the elongate surface, but maintaining the support members at the same rotational position. If the table 800 is desired to be maintained at an angled, or slanted, position, one of the support members 818 can be rotated to a different degree than the other support member.

An arm 852 can extend from a lower end 848 of each support member 818. A foot 856 can be disposed about each of the arms 852, such as by inserting a respective arm through an opening 860 axially formed in the arm. The feet 856 can be rotatable relative to the arms 852, such that the feet can rest on a surface, such as a horizontal surface, even when the support members 818 are not maintained in a vertical orientation. The feet 856 can be formed from a resilient material, such that a patient may comfortably lay on the feet, helping secure the table 800 in a desired position.

Various modifications can be made to the table 800. For instance, one or both of the coupling members 822 and the receptacles 836 can be rotatable. When one or both of the coupling members 822 and the receptacles 836 are rotatable, the components may be secured to one another, or be an integral component, if desired. A locking/release mechanism, such as a spring loaded pawl, can be used to engage teeth associated with the support members 818 in order to maintain each support member at a desired position. In some embodiments, the upper end portion of each support member 818 can be pivotably connected to the table 800, such as via a pivot pin extending through the upper end portion of each support member 818 and an adjacent portion of the table.

Figure 9:
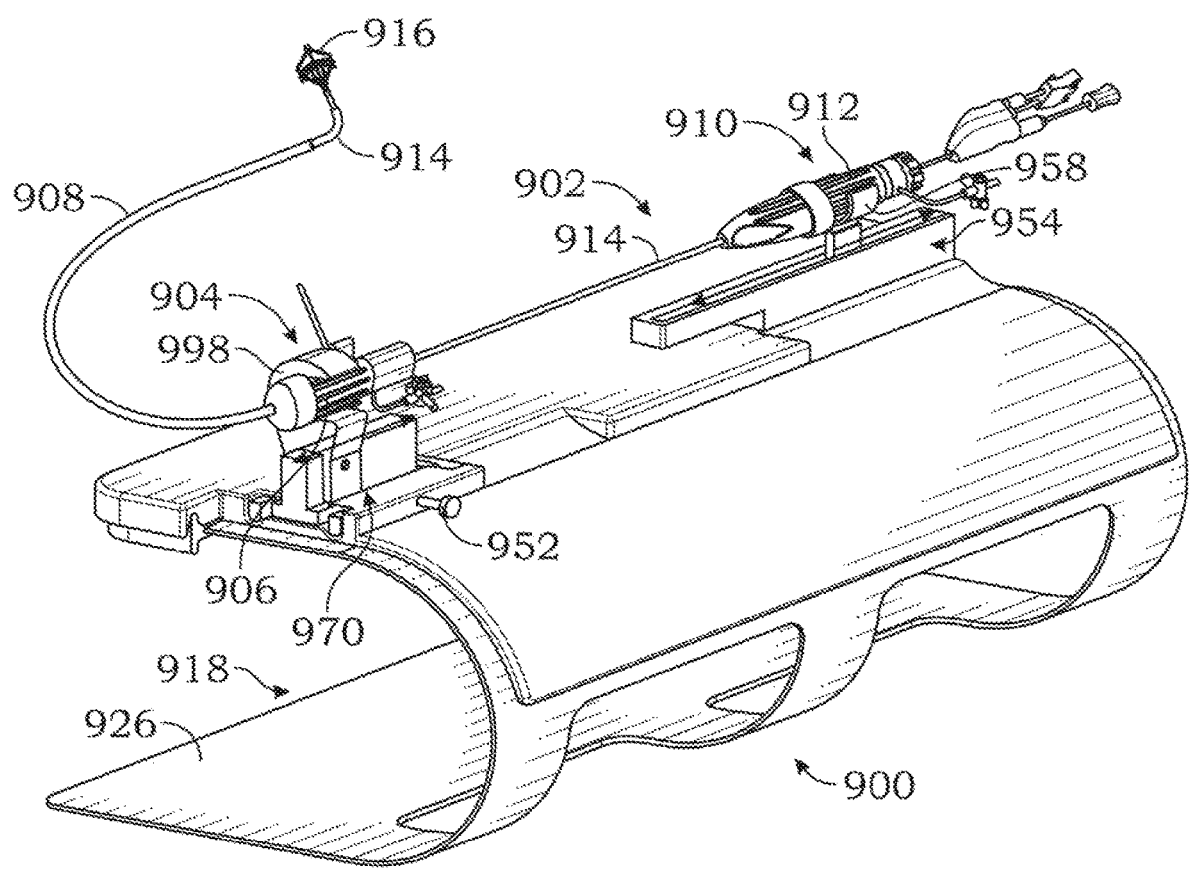
FIG. 9 is a perspective view of a support table and an embodiment of a stabilizing system useable with a medical device and having a rotatable locking member.

FIG. 9 illustrates a further embodiment of a stabilizing system, in the form of a stabilizing system 900 for a medical device 902. The stabilizing system 900 includes a U-shaped table or platform 918 on which one or more stabilizing units can be mounted. The illustrated embodiment includes a proximal stabilizing unit 954 and a distal stabilizing unit 970, both of which can be secured to the table 918.

The medical device 902 can be a transcatheter delivery system having a guide catheter 904 comprising a handle 906 and an elongated shaft 908 extending distally from the handle 906. A distal end of the shaft 908 can be inserted into the vasculature of a patient. The medical device 902 can further include a delivery catheter 910 comprising a handle 912 and an elongated shaft 914 extending distally from the handle 912. The shaft 914 can extend through a lumen of the shaft 908. An implantable prosthetic device 916 can be releasably coupled to the distal end of the shaft 914. The handle 906 can be securely and releasably retained in the distal stabilizing unit 970 using a rotatable locking member 998, as further described below. The handle 912 can be supported in a C-shaped support member 958 of the proximal stabilizing unit 954.

Although shown in use with the table 918, the stabilizing units 954, 970 can be used with other support surfaces, such as the table 108 of FIG. 1, a table constructed from the packaging sheet 300 of FIGS. 5a-c or the packing sheet 400 of FIG. 6, or the table 800 of FIG. 8. Similarly, the table 918 can be used with other stabilizing units, including the stabilizing unit 106 of FIG. 1 or the stabilizing unit 200 of FIG. 4. Additionally, in alternative embodiments, the system 900 can include a single stabilizing unit (either stabilizing unit 954 or 970), or multiple stabilizing units of the same type (e.g., multiple stabilizing units 954 or multiple stabilizing units 970). Also, the stabilizing units 954, 970 need not be positioned at the proximal and distal ends of the table. One or more stabilizing units can be positioned at any desired locations between the proximal and distal ends of the table in lieu of or in addition to the ones at the proximal and distal ends.

The medical device 902 can be used for delivering any of various types of implantable medical devices into a patient's body, including, without limitation, prosthetic valves (e.g., prosthetic heart valves), stents, stent-grafts, and various types of leaflet or valve repair devices, such as annuloplasty devices, leaflet clips, and the like. In the illustrated embodiment, the implantable device 916 comprises a valve repair device that is implanted on opposing leaflets of a native valve (e.g., a mitral valve) to reduce regurgitation through the native valve. In some implementations, the medical device 902 may comprise an assembly comprised of multiple catheters that are insertable into a patient's body (as shown in FIG. 9), or a single catheter.

Figure 10:
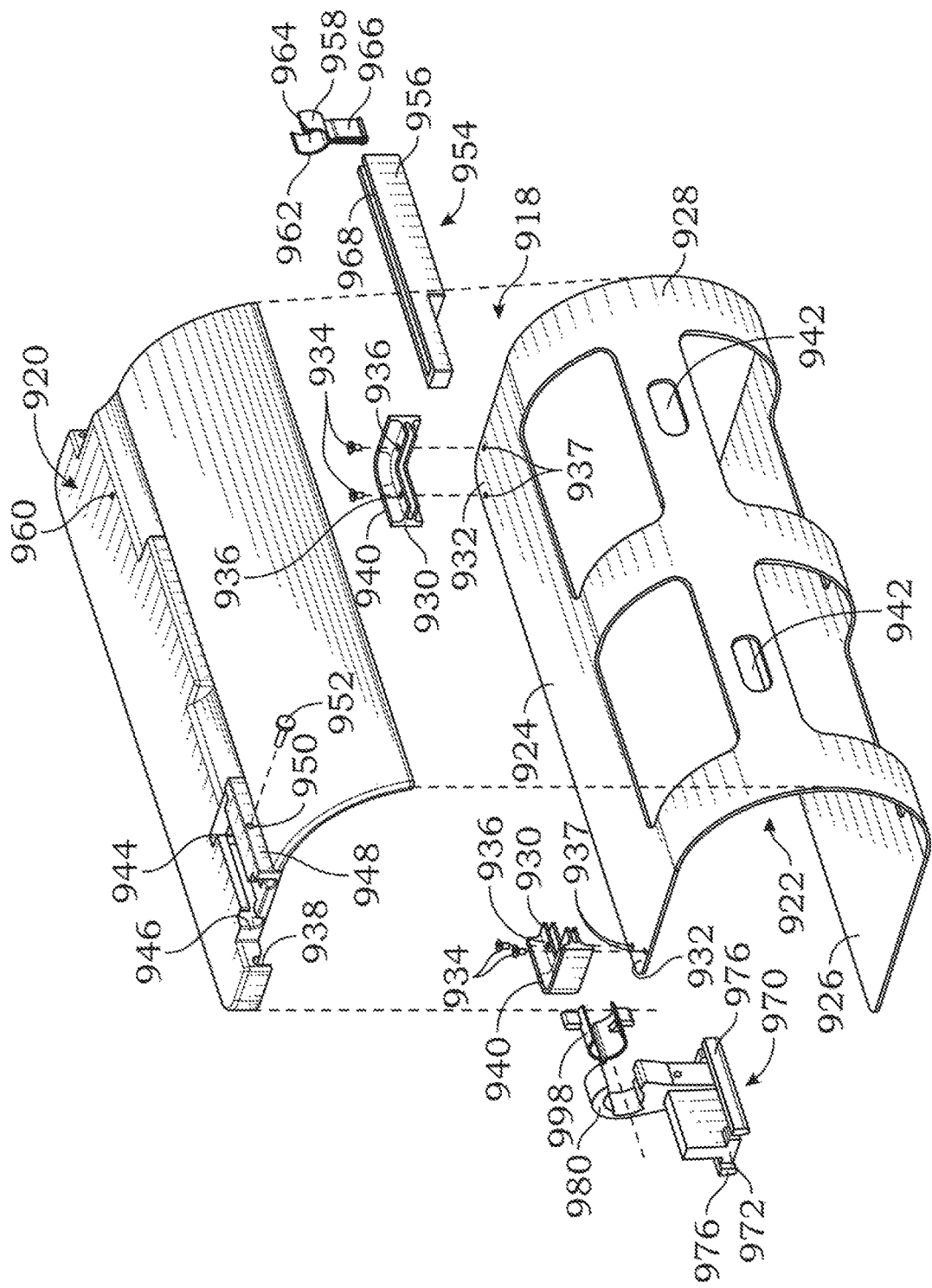
FIG. 10 is an exploded, perspective view of the table and stabilizing system of FIG. 9.

With reference to FIGS. 9 and 10, the table 918 can comprise an upper member 920 mounted on a base member 922. The base member 922 can comprise an upper portion 924, a lower portion 926, and a side portion 928 extending between the upper portion and the lower portion. The lower portion 926 can serve as a support for the table 918, such as when resting on a surface of an operating table. The upper member 920 and the base member 922 can be formed from a sterilizable, suitably rigid material, such as polycarbonate or high density polyethylene, other plastics, or metals.

The base member 922 has a generally C-shape in cross-sectional profile with an open side opposite the side portion 928 sized to receive the leg of a patient. The side portion 928 can be curved as shown in the figures to better conform to the leg of a patient. In use, the patient's leg is placed in the space bounded by the upper portion 924, the lower portion 926, and the side portion 928. The table 918 can be held in place relative to an operating table by the weight of the patient's leg on the lower portion 926. In other embodiments, the base member 922 can be sized to be placed around another body portion of the patient, depending on the particular procedure. For example, the base member can be sized to be placed around an arm patient.

A pair of brackets 930 can be used to secure the upper member 920 to the base member 922. The brackets 930 can be secured to outer corners 932 of the upper portion 924, such as by inserting fasteners 934 (e.g., screws) through apertures 936 formed in the brackets and apertures 937 formed in the outer corners 932. The upper member 920 of the table 918 can have slots 938 in a lower surface thereof that can placed over ridges 940 of the brackets 930. The slots 938 and ridges 940 can be in frictional engagement such that the upper member 920 is secured against movement in a horizontal plane with respect to the base member 922. In some cases, the slots 938 and ridges 940 can provide a "snap fit" engagement. The upper member 920 can be further secured to the base member 922 by inserting obround protrusions (not shown) through obround apertures 942 formed in the side portion 928 of the base member. In other cases, the upper member 924 can be secured to the base member 922 with fasteners (e.g., screws) in lieu of or in addition to the other attachment mechanisms previously described.

The upper member 920 can include a recessed portion 944 defining an inverted T-shaped slot 946 for use in mounting the distal stabilizing unit 970. A longitudinal side 948 of the recessed portion 944 can define an aperture 950 for receiving a fastener 952, such as a set screw or bolt.

The proximal stabilizing unit 954 can comprise a base portion 956 that supports a support member 958. The proximal stabilizing unit 954 can be secured to the upper member 920 of the table 918 by inserting a fastener (not shown) through an aperture 960 (FIG. 10) formed in the upper member 920 and into a mating aperture (not shown) of the base portion 956. The support member 958 can include an upper portion 962 defining an arcuate slot 964 and a lower portion 966 in the form of an inverted T-shaped arm. The bottom sides of the arm 966, being wider than the stem of the arm, can act as guide rails when inserted into a mating slot 968 formed in the longitudinal upper surface of the base portion 956. Although not shown in FIGS. 9 and 10, in some cases, the support member 958 can be secured at a desired longitudinal position in the slot 968 by inserting a fastener, such as a set screw or bolt, through an aperture in a side of the base portion 956 such that it engages an adjacent surface of the arm 966 or is tightened into a threaded aperture in the arm 966.

The upper portion 962 can have a generally C-shape in cross-sectional profile and can be open at the top to receive a medical device within the slot 964. For example, the upper portion 962 can be sized to receive the handle 912 of the delivery catheter 910, as depicted in FIG. 9. The diameter of the slot 968 can be slightly smaller than the outer diameter of the handle 912. In this manner, when the handle 912 is placed in the slot 968, the sides of the upper portion can flex or deflect away from each other and frictionally engage the sides of the handle 912.

Having a table 918 with a removable upper member 920 can provide various advantages. For example, the upper member 920 can be a sterile, disposable component, while the base member 922 can be reusable. Or, the upper member 920 can also be reusable, but the ability to disassemble the table 918 may facilitate sterilization of the upper member 920 or other table components. As a further example, base members 922 can be provided in multiple sizes. A medical practitioner can select an appropriately-sized base member 922 and assemble a table 918 by snapping an upper member 920 onto the selected abase member 922.

In alternative embodiments, the table 918 need not have a separate upper member 920 and instead the upper portion 920 of the base member 922 can have features (e.g., a recessed portion 944) for mounting the stabilizing units 954, 970. Or, the proximal stabilizing unit 954 or the distal stabilizing unit 970 may be mounted to the table 918 in another manner. For example, the slot 968 for receiving the arm 966 can be molded into the upper member 922 or the upper portion 924 of the base member 922. During assembly of the table 918, the arm 966 can be inserted into the slot

968. The arm 966 can be constructed from a resilient material such that it can snap into place within the slot 968.

In some aspects, a surgical drape can be secured between the upper member 920 and the base member 922, such as by placing portions of the drape between the slots 938 and the ridges 940. The surgical drape can be secured by the slots 938 and the ridges 940, but can also help maintain the slots and ridges in frictional engagement. The use of a surgical drape as described can help maintain a sterile surgical field above the drape.

FIGS. 11 and 12 are perspective views of the distal stabilizing unit 970. A base portion 972 of the stabilizing unit can comprise a lower portion 974 defining side rails 976 and an upper mounting portion 978 extending upwardly from the lower portion 974. The distal stabilizing unit 970 can further include a support member 980 supported on the mounting portion 978. The support member 980 is configured to receive and support the handle 906 of the guide catheter 904, as further described below.

The support member 980 can include a lower portion 982 in the form of a fork defining a U-shaped slot 984. The support member 980 can be mounted on the mounting portion 978 by placing the lower portion 982 over the mounting portion 978 such that the mounting portion 978 extends into the slot 984 (FIG. 12). The support member 980 can be longitudinally translatable relative to the mounting portion 978, and can be secured at a desired location on the mounting portion 978 by inserting a fastener (e.g., a screw; not shown), such as a set screw or bolt, through an aperture 986 formed in a lateral side of an arm 988 of the lower portion 982 and tightening the fastener against an adjacent surface of the mounting portion 978 or into a threaded aperture in the mounting portion 978.

With reference to FIG. 11, the arms 988 of the lower portion 982 can be longitudinally translated in longitudinally extending slots 990 formed in the lower portion 974 of the base portion 972. The lower end portions of the arms 988 can include laterally extending ridges 992 that can engage a lower surface of the base portion 972 and prevent the support member 980 from moving upwardly with respect to the base portion 972. In some cases, the slots 990 can include widened portions (not shown), such as at the ends of the slots, which are larger than the lower end portions of the arms 988 (the portions that include the ridges 992) to allow the arms 988 to be inserted into and removed from the slots 990 of the base portion 972.

The support member 980 can comprise a generally C-shaped upper portion 994 defining a lumen or slot 996 that is open on one side to receive the handle 906 (FIG. 9). With further reference to FIGS. 13 and 14, a rotatable locking member 998 can be mounted in the lumen 996. The locking member 998 is sized to extend at least partially around the handle 906 when it is placed within the lumen 996. The rotatable locking member 998 is configured to be rotated between a first, unlocked position in which the handle 906 can be easily inserted within the rotatable locking member 998 and a second, locked positon in which the rotatable locking member 998 engages the handle 906 and prevents inadvertent movement of the handle 906 relative to the distal stabilizing unit 970. The upper portion 994 of the support member 980 is configured to cooperate with the rotatable locking member 998 to produce radial compression of the rotatable locking member 998 against the handle 906 as the rotatable locking member 998 is rotated from the unlocked position to the locked position, as further described below.

Figure 15:
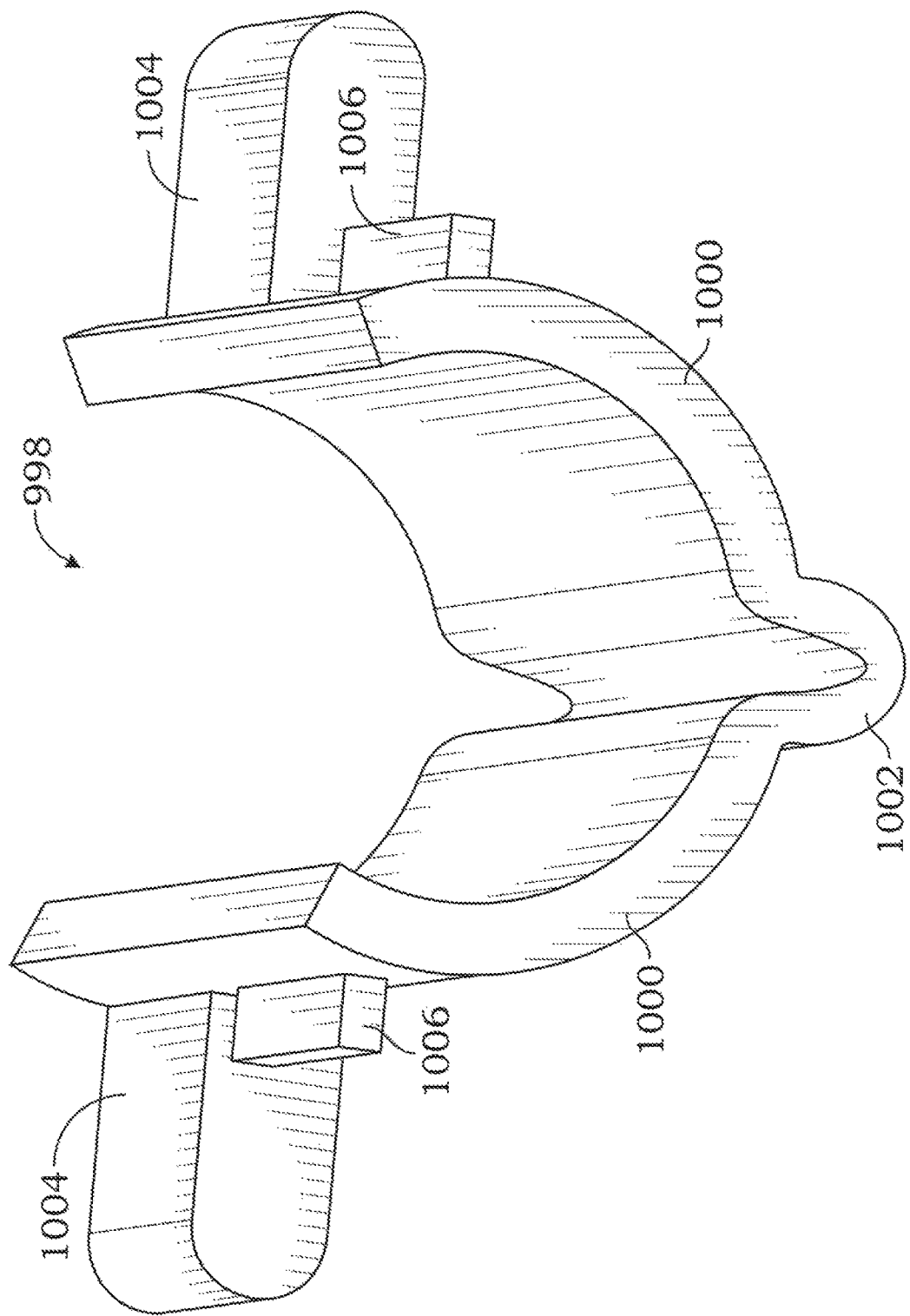
FIG. 15 is a perspective view of a rotatable locking member useable in the distal stabilizing unit of the stabilizing system of FIG. 9.

Referring to FIG. 15, the rotatable locking member 998 in the illustrated embodiment comprises a generally C-shaped body having two arcuate, semi-circular arms 1000 connected by a spring hinge 1002, such as in the form of a radially projecting hairpin or loop portion of the body. The rotatable locking member 998 can also include two handle portions 1004 and two nubs or protrusions 1006 projecting radially outwardly from the outer surfaces of the arms 1000. The handle portions 1004 facilitate manual rotation of the rotatable locking member 998 within the support member 980. The spring hinge 1002 allows the arms 1000 to be radially compressed toward each other to a radial compressed state during locking and biases the arms 1000 away from each other to a radially expanded state during unlocking of the locking member. The protrusions 1006 cooperate with features in the lumen 996 of the support member 980 to produce radial compression of the locking member and allow for radial expansion of the rotatable locking member 998 under the bias of the spring hinge 1002 when it is rotated between the locked and unlocked positions, as further described below.

The rotatable locking member 998 in the illustrated embodiment comprises a one-piece, unitary body, although it can have other configurations. For example, the arms 1000 and the spring hinge 1002 can be separate components that are coupled to each other using various types of hinge connections. For example, the arms 1000 can be pivotably connected to each other with a pivot pin extending through adjacent ends of the arms and a separate spring (e.g., a torsion spring) or other type of biasing element can be coupled to the arms to bias the arms to the radially expanded state.

Figure 16:
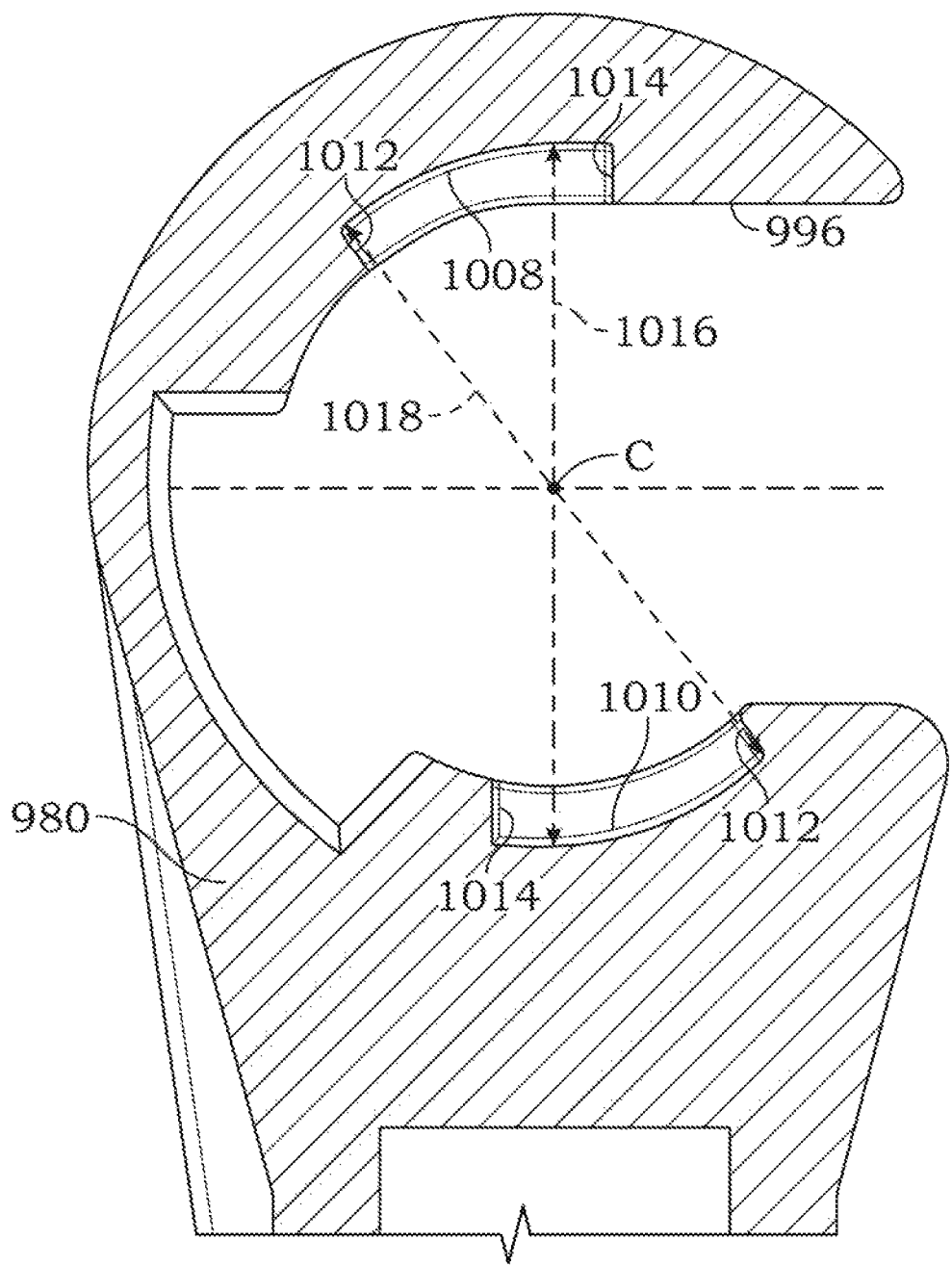
FIG. 16 is a cross-sectional view of an upper portion of a support member of the distal stabilizing unit of FIGS. 11 and 12.

As best shown in FIG. 16, the inner surface of the lumen 996 can be formed with slots or track portions 1008, 1010 that receive the protrusions 1006 of the rotatable locking member 998. The track portions 1008, 1010 can be shaped such that the distance measured between opposing locations on the tracks varies along the tracks to produce radial compression of locking member 998 as the protrusions 1006 are rotated within the tracks 1008, 1010. In the illustrated embodiment, for example, the tracks 1008, 1010 follow the shape of an ellipse. The tracks 1008, 1010 therefore can be referred to as partial elliptical tracks. The tracks 1008, 1010 can have opposing end surfaces 1012, 1014 that limit rotation of the protrusions 1006 within the tracks.

By virtue of their elliptical shape, the distance between opposing locations on the tracks 1008, 1010 measured along a first line 1016 intersecting a central axis C of the tracks is greater than the distance between opposing locations on the tracks measured along a second line 1018 intersecting the central axis C. The first line 1016 can be referred to as the major axis of the tracks 1008, 1010, having a first diameter, and the second line 1018 can be referred to as the minor axis of the tracks 1008, 1010, having a second diameter less than the first diameter.

As best shown in FIGS. 13 and 14, the lumen 996 can further define a cutout portion 1020 located circumferentially between the track portions 1008, 1010 and having a larger diameter than adjacent portions of the lumen. In at least some cases, the cutout portion 1020 can extend the entire length of the lumen 996 between the axial faces 1022, 1024 of the support member 980, while in other cases the cutout portion 1020 can extend less than the entire length of the lumen, and need not intersect the axial faces 1022, 1024 (FIG. 12) of the support member. The cutout portion 1020 can be sized to receive the spring hinge 1002 of the rotatable locking member 998.

As noted above, the locking member 998 is rotatable within the lumen 996 in the directions indicated by doubleheaded arrow 1026 in FIG. 13. When the locking member 998 is in the unlocked position (shown in FIG. 13), the protrusions 1006 can be located in portions of the track portions 1008, 1010 having the largest diameter (the protrusions are aligned along the major axis 1016). In this position, the spring hinge 1002 is in an uncompressed state, and the locking member 998 is open to its largest diameter and allows the handle 906 of the guide catheter 904 to be easily inserted into the locking member between the arms 1000. As the locking member 998 is rotated to the locked position (which is the clockwise direction in FIG. 13), the protrusions 1006 are pushed radially inwardly by virtue of the decreasing diameter of the track portions 1008, 1010. The spring hinge 1002 allows the diameter of the locking member 998 to be reduced, reaching a smallest diameter in the locked position shown in FIG. 14.

In the locked position, the protrusions 1006 are aligned along the minor axis 1018 of the track portions 1008, 1010 and the arms 1000 of the locking member 998 frictionally engage the outer surface of the handle 906. In particular embodiments, the frictional engagement between the locking member 998 and the handle 906 is sufficient to prevent inadvertent rotational and axial movement of the handle 906 relative to the distal stabilizing unit 970. When the locking member 998 is rotated from the locked position to the unlocked position (counterclockwise in FIG. 14), the arms 1000 can radially expand away from each other and the outer surface of the handle 906 under the bias of the spring hinge 1002.

If desired, the locking member 998 can include additional features to help secure the handle 906 in position. For instance, as best shown in FIGS. 11 and 12, the rotatable locking member 998 can include radially-inwardly directed projections 1028. The projections 1028 can be made from a resilient material and can provide additional frictional engagement with the handle 906. In further aspects, the projections 1028 can be positioned and dimensioned to engage features in an outer surface of the handle 906. For example, the handle 906 can include slots or other openings for receiving the projections 1028.

In some embodiments, the arms 1000 of the locking member 998 need not frictionally engage the outer surface of the handle 906 and instead the arms can include projections or other features that mate with corresponding features on the catheter 904 to resist movement of the catheter relative to the stabilizing unit 970. For example, the stabilizing unit 970 can retain the catheter 904 by virtue of the projections 1028 extending into corresponding slots or openings on the handle 906 without the arms 1000 exerting a clamping force against the handle 906.

In some embodiments, the locking member 998 can have more than two protrusions 1006 and the lumen 996 can be formed with more than two tracks, with each track configured to receive a corresponding protrusion. Also, in some embodiments, one of the tracks 1008, 1010 can be a different shape than the other. For example, one of the tracks 1008, 1010 can be an elliptical track as shown and the other track 1008, 1010 can be a circular track. In that case, the arm 1000 adjacent the elliptical track is moved radially inwardly and the arm 1000 adjacent the circular track is not moved radially inwardly when the locking member is rotated to the locked position, but the movement of the one arm is sufficient to clamp and/or engage a mating feature on the handle 906.

The locking member 998 can include features to help maintain a locked or unlocked configuration. As best shown in FIGS. 11 and 12, the elliptical track portion 1008 can include a radially outwardly extending notch 1030. The radially extending notch 1030 can be configured to receive a nub 1006 when the rotatable locking member 998 is rotated to a fully unlocked configuration (e.g., as shown in FIG. 13) to help retain the locking member 998 in the unlocked configuration. The nub 1006 can be removed from the notch 1030 by manually compressing the rotatable locking member 998, such as by applying a radially inwardly directed force using the handles 1004. In some configurations, only one of the tracks 1008, 1010 can include a notch or similar feature to receive a nub 1006 and help maintain an unlocked configuration. Alternatively, both of the tracks 1008, 1010 can include a notch or similar feature to help maintain the rotatable locking member 998 in the unlocked configuration. In further aspects, the lumen of the support member 980 can include features that engage or mate with the nubs 1006 or other portions of the locking member 998 to help retain the locking member in the locked position.

In use, the table 918 can be placed around a patient's leg (e.g., with the lower or upper portion of the patient's leg resting on the lower portion 926 of the table). Positioning the table 918 around the leg of the patient allows the catheters 904, 910 to be roughly aligned with the inner thigh of the patient to facilitate insertion of the catheters into the femoral vein or femoral artery of the same leg.

The distal stabilizing unit 970 can be mounted to the upper member 920 of the table 918 by sliding the side rails 976 into the slot 946 of the recessed portion 944 of the upper member 920. The distal stabilizing unit 970 can be secured within the recessed portion 944 by tightening the fastener 952 such that it frictionally engages an adjacent side rail 976 or extends into a threaded aperture in the adjacent side rail. As best shown in FIGS. 11 and 12, the lower portion 982 of the support member 980 can be slid over the mounting portion 978 to a desired longitudinal position along the length of the mounting portion. The lower portion 982 can be secured at the desired longitudinal position by inserting a set screw (not shown) through the aperture 986 such that it frictionally engages the mounting portion 978 or extends into a threaded aperture in the mounting portion.

It should be noted that one or more of the components of the table 918 and the stabilizing units 954, 970 can be assembled by the manufacturer and/or the end user, depending on whether certain components are one-use, disposable components or are sterilized and re-used after each medical procedure. In certain examples, the table 918 and the stabilizing units 954, 970 can be packaged and sold fully assembled and the end user can adjust the longitudinal positions of the stabilizing units 954, 970 as needed prior to a medical procedure. In some examples, the table 918 can be packaged and sold separately from any stabilizing units, which can allow the end user to select one or more stabilizing units 954, 970 needed for a particular procedure.

Further, in some aspects, the table 918 can be provided with multiple base members 922 having a range of heights between the upper portion 924 and the lower portion 926. The base members 922 can be stacked inside one another to facilitate packaging and shipping. A medical practitioner can select the base member 922 having the appropriate height, such as based on the size of a patient's leg. For example, by selecting the appropriately sized base member 922, the medical practitioner can control the insertion angle of a medical device, such as a catheter, relative to a patient's femoral artery. The table 918 can then be assembled by snapping the upper member 920 onto the selected base member 922.

In further aspects, the base member 922 can have an adjustable height between the upper portion 924 and the lower portion 926, including a mechanically adjustable height. For example, the upper portion 924 and the lower portion 926 may be generally L-shaped components that are slidable with respect to one another. During assembly of the table 918, the upper and lower portions 924, 926 can be slid relative to one another to provide a desired separation between the upper portion 924 and the lower portion 926. The upper portion 924 and the lower portion 926 can then be secured relative to one another, such as by using a fastener (for example, a set screw), a clamp, or by inserting protrusions of one portion into mating slots of the other portion. In further aspects, the table 918 height may be adjusted in another manner.

With reference to FIGS. 13 and 14, during a medical procedure, a medical practitioner can place the handle 906 of the catheter 904 in the stabilizing unit 970 when the locking member 998 is in the unlocked or "open" position (FIG. 13). If needed, the medical practitioner can rotate the locking member 998 to the unlocked position. The handle 906 can then be inserted through the side opening 984 of the support member 980 and placed between the arms of the locking member 998. While the catheter 904 is supported by the stabilizing unit 970 with the locking member 998 in the unlocked position, the user can move the catheter distally into and through the patient's vasculature and/or move the catheter 904 proximally to withdraw or retract the catheter relative to the patient's vasculature. Once the distal end portion of the catheter 904 is advanced to a desired location within the patient's body (e.g., within the heart if performing a procedure within a heart chamber), the position of the catheter 904 can be retained by rotating the locking member 998 to the locked or "closed" position, so that the locking member 998 clamps or otherwise restricts movement (rotational and/or axial movement) of the handle 906 within the locking member, as described above. The medical practitioner may repeat this locking and unlocking process as desired during a medical procedure in order to reposition (e.g., rotate or translate) the catheter 904.

The stabilizing unit 970 is described above in the context of retaining the handle 906 of a catheter 904. It should be noted that the components of the stabilizing unit 970, and in particular the lumen 984 of the support member 980 and the locking member 998 can be appropriately sized to retain another portion of the catheter 904 (e.g., the shaft 908) or another type of medical device.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and sub-combinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Accordingly, the scope of the invention is defined by the following claims. We therefore claim as our invention all that comes within the scope and spirit of these claims.

We claim:

1. A system for a medical device, comprising:
   a stabilizing apparatus, comprising:
      a housing;
      a retaining arm coupled to the housing;
      a moveable stabilizing fork slidably disposed within the housing, the stabilizing fork comprising a slot configured to receive the medical device; and
      a biasing member configured to urge the slot of the stabilizing fork towards the retaining arm; and
   a table configured to serve as packaging for the medical device during shipping of the medical device, wherein the stabilizing apparatus is coupleable to the table;
   wherein, when the medical device is placed in the slot of the stabilizing fork, the biasing member urges the stabilizing fork against a first portion of the medical device, and a second portion of the medical device against the retaining arm.

2. The system of claim 1, wherein the slot of the stabilizing fork comprises a plurality of ridges configured to engage a handle of the medical device.

3. The system of claim 1, wherein the stabilizing fork is slidable in a first direction against a biasing force of the biasing member and the retaining arm is slidable over the slot of the stabilizing fork in a second direction that is lateral to the first direction.

4. The system of claim 1, wherein the retaining arm is pivotably coupled to the housing.

5. The system of claim 1, wherein the stabilizing apparatus is coupleable to the table with a clamp.

6. The system of claim 1, wherein a base of the stabilizing apparatus comprises an arm having a recess adapted to receive a coupling member to couple the stabilizing apparatus to the table.

7. The system of claim 1, wherein a base of the stabilizing apparatus comprises an arm having a recess adapted to receive a coupling member and the table comprises a ridge, wherein when the arm is placed under the ridge, a side of the recess is aligned with an outer edge of the ridge.

8. The system of claim 1, wherein the table is formed from a folded elongate member.

9. The system of claim 1, wherein the table includes a recess for receiving a handle of the medical device for storing the medical device during shipping.

10. A stabilizing apparatus for a medical device, comprising:
a housing;
a retaining arm coupled to the housing;
a movable stabilizing fork slidably disposed within the housing, the stabilizing fork comprising a slot configured to receive the medical device; and
a biasing member configured to urge the slot of the stabilizing fork towards the retaining arm;
wherein, when the medical device is placed in the slot of the stabilizing fork, the biasing member urges the stabilizing fork against an adjacent surface of the medical device, and an opposing surface of the medical device against the retaining arm, wherein the stabilizing fork is slidable in a first direction against a biasing force of the biasing member and the retaining arm is slidable over the slot of the stabilizing fork in a second direction that is lateral to the first direction.

11. The stabilizing apparatus of claim 10, wherein the slot of the stabilizing fork comprises a plurality of ridges configured to engage a handle of the medical device.

12. The stabilizing apparatus of claim 10, wherein the retaining arm is pivotably coupled to the housing.

13. The stabilizing apparatus of claim 10, further comprising a table, wherein the housing is coupled to a base that can be disposed on the table and coupled to the table.

14. The stabilizing apparatus of claim 13, wherein the base is coupled to the table with a clamp.

15. The stabilizing apparatus of claim 13, wherein the base comprises an arm having a recess adapted to receive a coupling member to couple the base to the table.

16. The stabilizing apparatus of claim 13, wherein the base comprises an arm having a recess adapted to receive a coupling member and the table comprises a ridge, wherein when the arm is placed under the ridge, a side of the recess is aligned with an outer edge of the ridge.

17. The stabilizing apparatus of claim 13, wherein the table is formed from a folded elongate member.

18. The stabilizing apparatus of claim 10, wherein the stabilizing fork comprises arms separated by the slot and the retaining arm comprises an aperture through which an upper end portion of at least one of the arms extends.

19. A stabilizing apparatus for a medical device, comprising:
a housing;
a retaining arm coupled to the housing;
a table, wherein the housing is coupled to a base that can be disposed on the table and coupled to the table;
a movable stabilizing fork slidably disposed within the housing, the stabilizing fork comprising a slot configured to receive the medical device; and
a biasing member configured to urge the slot of the stabilizing fork towards the retaining arm;
wherein, when the medical device is placed in the slot of the stabilizing fork, the biasing member urges the stabilizing fork against an adjacent surface of the medical device, and an opposing surface of the medical device against the retaining arm; and
wherein the table is configured to serve as packaging for the medical device during shipping of the medical device.

20. A system for stabilizing a medical device, comprising:
a stabilizing apparatus, comprising:
a housing;
a retaining arm coupled to the housing;
a moveable stabilizing fork slidably disposed within the housing, the stabilizing fork comprising a slot configured to receive the medical device; and
a biasing member configured to urge the slot of the stabilizing fork towards the retaining arm;
wherein, when the medical device is placed in the slot of the stabilizing fork, the biasing member urges the stabilizing fork against a first portion of the medical device, and a second portion of the medical device against the retaining arm; and
wherein the stabilizing fork is slidable in a first direction against a biasing force of the biasing member and the retaining arm is slidable over the slot of the stabilizing fork in a second direction that is lateral to the first direction.

21. The system of claim 20, wherein the slot of the stabilizing fork comprises a plurality of ridges configured to engage a handle of the medical device.

22. The system of claim 20, wherein the retaining arm is pivotably coupled to the housing.

23. The system of claim 20, further comprising a table, wherein the stabilizing apparatus can be disposed on the table with a base of the stabilizing apparatus coupled to the table.

24. The system of claim 23, wherein the stabilizing apparatus is coupleable to the table with a clamp.

25. The system of claim 23, wherein the base comprises an arm having a recess adapted to receive a coupling member to couple the stabilizing apparatus to the table.

26. The system of claim 23, wherein the base comprises an arm having a recess adapted to receive a coupling member and the table comprises a ridge, wherein when the arm is placed under the ridge, a side of the recess is aligned with an outer edge of the ridge.

27. The system of claim 23, wherein the table is formed from a folded elongate member.

28. The system of claim 20, wherein the stabilizing fork comprises arms separated by the slot and the retaining arm comprises an aperture through which an upper end portion of at least one of the arms extends.

29. A system for stabilizing a medical device, comprising:
a stabilizing apparatus, comprising:
a housing;
a retaining arm coupled to the housing;
a moveable stabilizing fork slidably disposed within the housing, the stabilizing fork comprising a slot configured to receive the medical device; and a biasing member configured to urge the slot of the stabilizing fork towards the retaining arm;

wherein, when the medical device is placed in the slot of the stabilizing fork, the biasing member urges the stabilizing fork against a first portion of the medical device, and a second portion of the medical device against the retaining arm; and a table;

wherein the stabilizing apparatus can be disposed on the table with a base of the stabilizing apparatus coupled to the table;

wherein the table is configured to serve as packaging for the medical device during shipping of the medical device.

30. A stabilizing apparatus for a medical device, comprising:

a housing;

a retaining arm coupled to the housing;

a movable stabilizing fork slidably disposed within the housing, the stabilizing fork comprising a slot configured to receive the medical device; and a spring configured to urge the slot of the stabilizing fork towards the retaining arm;

wherein, when the medical device is placed in the slot of the stabilizing fork, the spring urges the stabilizing fork against an adjacent surface of the medical device, and an opposing surface of the medical device against the retaining arm; and wherein the stabilizing fork is slidable in a first direction against a biasing force of the spring and the retaining arm is slidable over the slot of the stabilizing fork in a second direction that is lateral to the first direction.

31. The stabilizing apparatus of claim 30, wherein the slot of the stabilizing fork comprises a plurality of ridges configured to engage a handle of the medical device.

32. The stabilizing apparatus of claim 30, wherein the retaining arm is pivotably coupled to the housing.

33. The stabilizing apparatus of claim 30, further comprising a table, wherein the housing is coupled to a base that can be disposed on the table and coupled to the table.

34. The stabilizing apparatus of claim 33, wherein the base is coupled to the table with a clamp.

35. The stabilizing apparatus of claim 33, wherein the base comprises an arm having a recess adapted to receive a coupling member to couple the base to the table.

36. The stabilizing apparatus of claim 33, wherein the base comprises an arm having a recess adapted to receive a coupling member and the table comprises a ridge, wherein when the arm is placed under the ridge, a side of the recess is aligned with an outer edge of the ridge.

37. The stabilizing apparatus of claim 33, wherein the table is formed from a folded elongate member.

38. The stabilizing apparatus of claim 33, wherein the table is configured to serve as packaging for the medical device during shipping of the medical device.

39. A system for stabilizing a medical device, comprising:

a stabilizing apparatus, comprising:

a housing;

a retaining arm coupled to the housing;

a moveable stabilizing fork slidably disposed within the housing, the stabilizing fork comprising a slot configured to receive the medical device; and a spring configured to urge the slot of the stabilizing fork towards the retaining arm;

wherein, when the medical device is placed in the slot of the stabilizing fork, the spring urges the stabilizing fork against a first portion of the medical device, and a second portion of the medical device against the retaining arm; and wherein the stabilizing fork is slidable in a first direction against a biasing force of the spring and the retaining arm is slidable over the slot of the stabilizing fork in a second direction that is lateral to the first direction.

40. The system of claim 39, wherein the slot of the stabilizing fork comprises a plurality of ridges configured to engage a handle of the medical device.

41. The system of claim 39, wherein the retaining arm is pivotably coupled to the housing.

42. The system of claim 39, further comprising a table, wherein the stabilizing apparatus can be disposed on the table with a base of the stabilizing apparatus coupled to the table.

43. The system of claim 42, wherein the stabilizing apparatus is coupleable to the table with a clamp.

44. The system of claim 42, wherein the base comprises an arm having a recess adapted to receive a coupling member to couple the stabilizing apparatus to the table.

45. The system of claim 42, wherein the base comprises an arm having a recess adapted to receive a coupling member and the table comprises a ridge, wherein when the arm is placed under the ridge, a side of the recess is aligned with an outer edge of the ridge.

46. The system of claim 42, wherein the table is formed from a folded elongate member.

47. The stabilizing apparatus of claim 42, wherein the table is configured to serve as packaging for the medical device during shipping of the medical device.

* * * * *